United States Patent [19]

Mushabac

[11] Patent Number: 5,347,454
[45] Date of Patent: Sep. 13, 1994

[54] METHOD, SYSTEM AND MOLD ASSEMBLY FOR USE IN PREPARING A DENTAL RESTORATION

[76] Inventor: David R. Mushabac, 919 Ocean Ave., Brooklyn, N.Y. 11226

[21] Appl. No.: 569,923

[22] Filed: Aug. 21, 1990

Related U.S. Application Data

[63] Continuation-in-part of Ser. No. 507,162, Apr. 10, 1990, and Ser. No. 526,512, May 21, 1990, Pat. No. 5,224,049.

[51] Int. Cl.⁵ .............................................. G06F 15/42
[52] U.S. Cl. .................... 364/413.280; 364/474.05
[58] Field of Search .................... 364/413.28, 474.05, 364/474.24; 433/214, 223

[56] References Cited

U.S. PATENT DOCUMENTS

| | | |
|---|---|---|
| 3,971,133 | 7/1976 | Mushabac . |
| 4,149,246 | 4/1979 | Goldman . |
| 4,182,312 | 1/1980 | Mushabac . |
| 4,239,431 | 12/1980 | Davini . |
| 4,349,277 | 9/1982 | Mundy et al. . |
| 4,431,420 | 2/1984 | Adair . |
| 4,436,684 | 3/1984 | White . |
| 4,525,858 | 6/1985 | Cline et al. . |
| 4,564,295 | 1/1986 | Halioua . |
| 4,575,805 | 3/1986 | Moermann et al. . |
| 4,577,968 | 3/1986 | Makosch . |
| 4,598,376 | 7/1986 | Burton et al. . |
| 4,611,288 | 9/1986 | Duret et al. . |
| 4,657,394 | 4/1987 | Halioua . |
| 4,663,720 | 5/1987 | Duret et al. . |
| 4,837,732 | 6/1989 | Brandestini et al. . |
| 4,936,862 | 6/1990 | Walker et al. . |
| 4,941,826 | 7/1990 | Loran et al. . |
| 5,027,281 | 6/1991 | Rekow et al. . |
| 5,092,022 | 3/1992 | Duret ............................. 364/474.05 |
| 5,128,870 | 7/1992 | Erdman et al. ................. 364/474.05 |
| 5,224,049 | 6/1993 | Mushabac ....................... 364/413.28 |

OTHER PUBLICATIONS

"Optical Methods to Measure Shape and Size," P. M. Boone *Adv. Dent. Res.* 1(1):27–38, Oct., 1987.

"Optical Methods to Measure Shape and Size," P. M. Boone (paper) no date known.

*Primary Examiner*—Robert A. Weinhardt
*Attorney, Agent, or Firm*—R. Neil Sudol; Henry D. Coleman

[57] ABSTRACT

A system for use in preparing a dental prosthesis comprises a signal generator for generating an electrical signal encoding geometric specifications of a dental prosthesis, the specifications including dimensions and shape of a tooth preparation at a dental site at which the prosthesis is to be affixed and configuration of the prosthesis. The system further comprises a robot mechanism for placing a first mold component and a second mold component, selected in accordance with the electrical signal, in predetermined relative positions to form a mold cavity, the first mold component corresponding in shape and dimensions to the tooth preparation. The system also comprises a filling device, a furnace and a computer. The filling device serves to introduce into the mold cavity a quantity of a fluidic solidifiable dental material such as a liquid or liquifiable precious metal or alloy or composite material. The metal or alloy may be in any of a number of equivalent forms, for example, powder, pellets or ingots. The robot mechanism and the filling device are at least partially disposed inside the furnace. The computer is operatively connected to the robot mechanism and the filling device for controlling and sequencing the operation thereof.

5 Claims, 18 Drawing Sheets

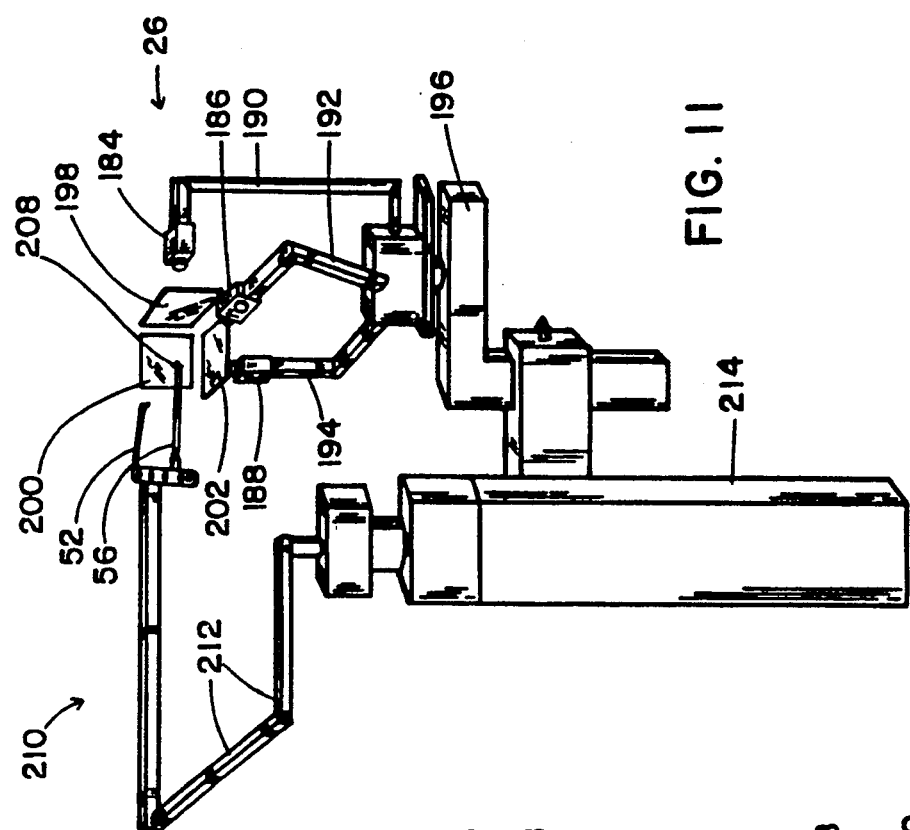
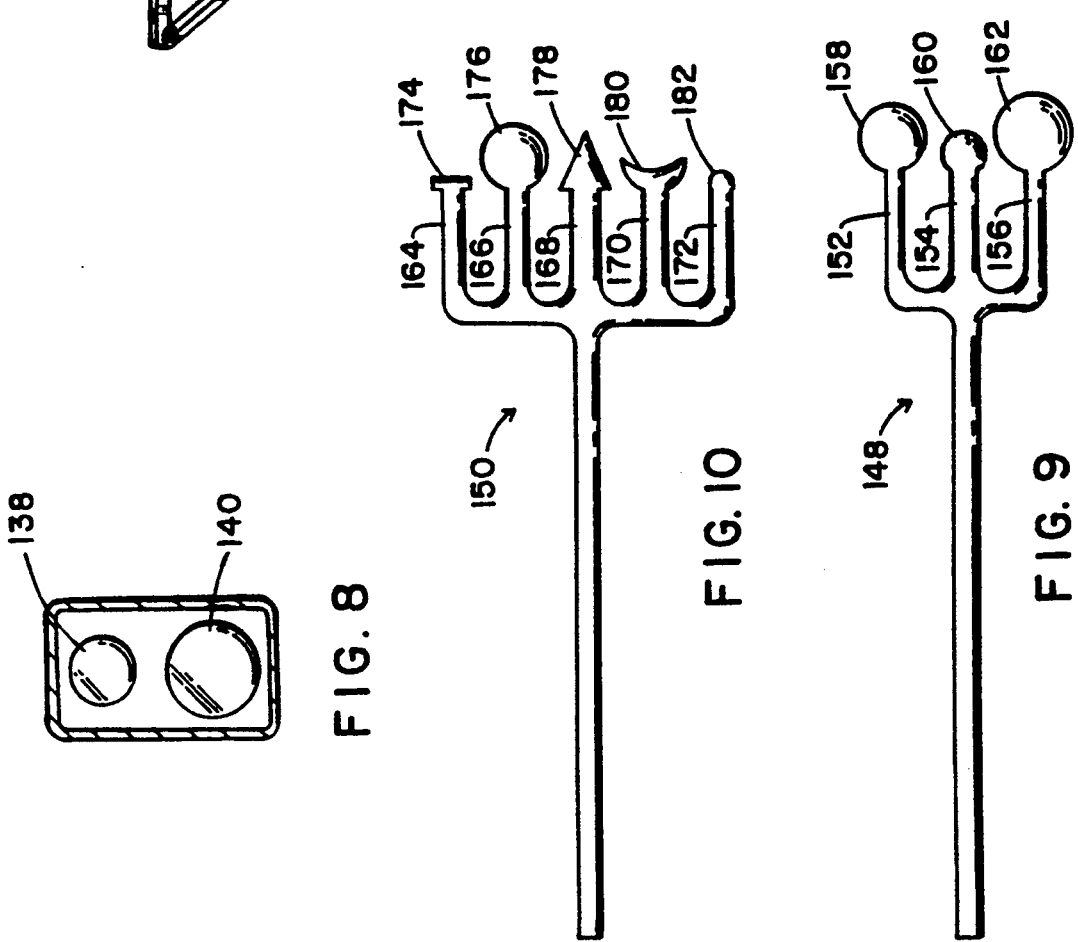
FIG. 11
FIG. 8
FIG. 10
FIG. 9

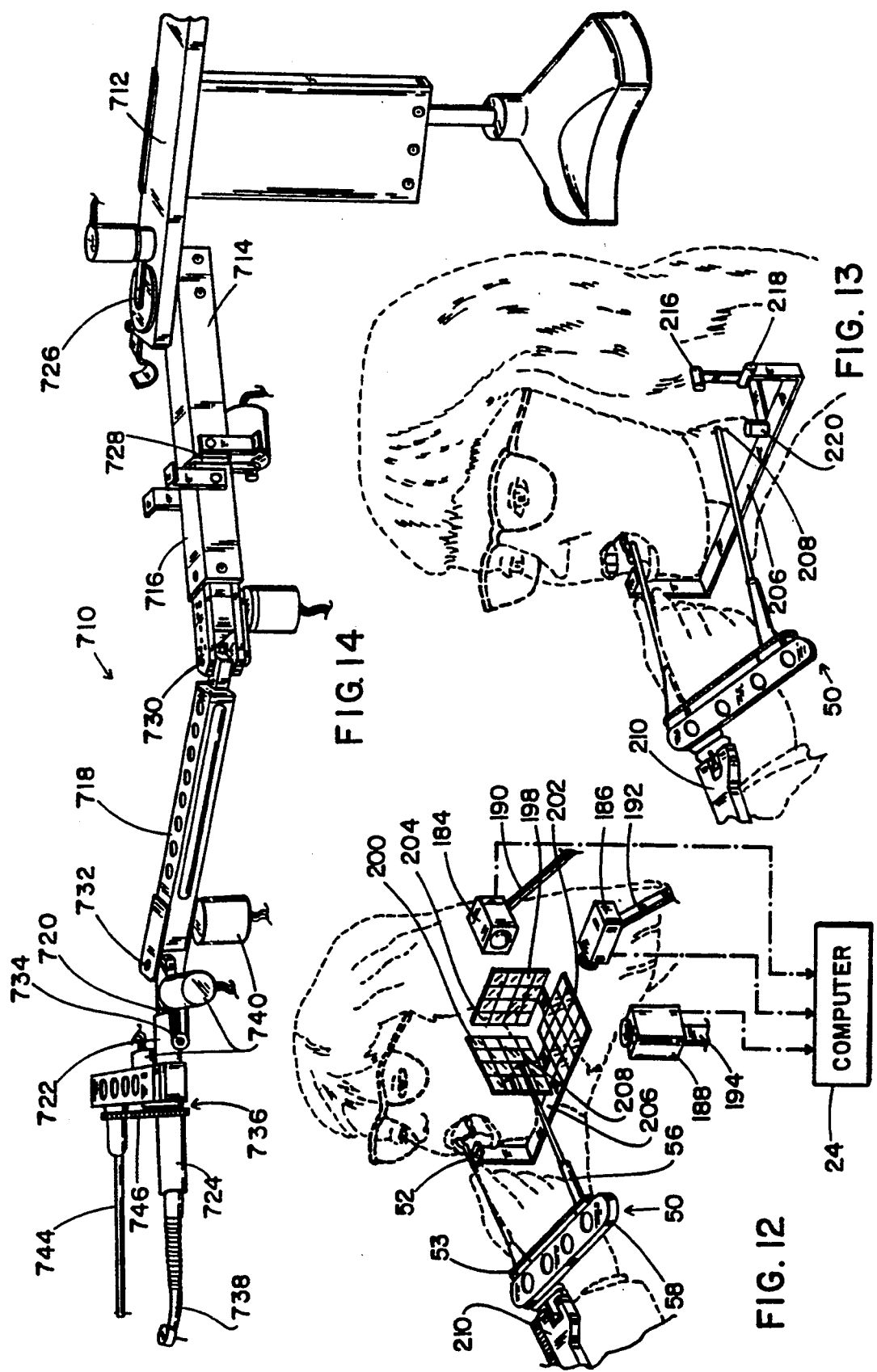

METHOD, SYSTEM AND MOLD ASSEMBLY FOR USE IN PREPARING A DENTAL RESTORATION

CROSS-REFERENCE TO A RELATED APPLICATIONS

This application is a continuation-in-part of applications Ser. No. 507,162 filed Apr. 10, 1990 and Ser. No. 526,512 filed May 21, 1990, now U.S. Pat. No. 5,224,049.

BACKGROUND OF THE INVENTION

This invention relates to method for preparing a dental restoration such as a prosthesis. This invention also relates to an apparatus or system for use in carrying out the method. In addition, this invention relates to a mold assembly for preparing a dental restoration or prosthesis.

In accordance with conventional techniques for providing a dental patient with a prosthetic overlay such as a crown, bridge or splint, a dental practitioner grinds the subject tooth or teeth down to form one or more tooth preparations to which the prosthetic device is to be attached. An impression of the tooth preparation or tooth preparations is taken in an elastic material and the impression is used to produce a model with dies. This in turn has a wax shape built to fit the die, so that a metal casting can be processed via the lost wax technique. The metal casting is then provided with a porcelain layer.

This method of casting for manufacturing prosthetic dental devices is labor intensive and, accordingly, expensive. In addition, the time required to make a dental prosthesis by such labor intensive methods is substantial and thus results in considerable delay in providing patients with crowns, bridges and splints.

The metal castings for the prosthetic devices are generally made by dental laboratories from metals or alloys purchased in the form of small ingots. After applying porcelain cover layers to the metal castings, the laboratories ship the finished prosthetic products to the dental practitioners who ordered them.

The manufacture of customized dental prostheses entails substantial efforts and time expenditures by dental laboratories to customize the fit of the castings, resulting in a reduction in value of the precious metal and a using of amounts of precious metals in the process that is lost in castings, grindings. The casting system is subject to so many variables as waxing thicknesses, investment expansions, metal homogenities that there are necessarily inaccuracies and errors in castings results, increased expense in the delivery of what is required and delay in the finalized, correctly fitted prosthetic dental devices. addition, it is frequently necessary for the dental technicians to hand shape required margins as well as eliminate small bubbles from the metal castings and to grind both internal and external surfaces of the prosthetic appliance in preparation for use and insertion in in the patients' mouths. This grinding away of expensive precious metal or any other metals is time consuming and results in inaccuracies, modifications of fit, and higher costs for precious metals.

In producing bridges or splints pursuant to traditional methods, the bridges or splints are frequently fabricated by using the excess materials of several prior castings, these prior castings being the excess of the sprued units. This manufacturing technique, as discussed above, is labor intensive and therefore results in high costs. In addition, in cases where there are soldered joints in a prosthetic dental device there is an unequal distribution of stress responsive forces throughout the device, and as a consequence multi-unit cases may be subject to failure due to porosity and/or fatigue at the soldered joints. Moreover, gases are generated in the casting and/or soldering process and such gases remain in the metal and are released and weaken the procelain when that material is baked onto the metal.

Because handheld grinding and/or drilling of the metal castings naturally results in reduced accuracies in the shapes of the final products and because conventional techniques for manufacturing dental prostheses such as crowns, bridges and splints are subject to continuous variables from the impression stage, to the modeling, waxing, casting and handheld grinding, a goodly number of dental prostheses are frequently ill-fitting or require multiple corrective steps, which gives rise to further variables, delays and cost increases.

New methodologies based on CAD/CAM and CAE design have recently been introduced. These new methodologies represent the only significant advance in the dental arts for centuries. Pursuant to the new techniques, a dental prosthesis such as a bridge is machined or milled from a solid chunk of material under computer control. The milling is of both internal and external surfaces of adjacent dental substructures and proceeds generally from tooth position to tooth position. Upon reaching the final tooth position in a bridge array, numerous inaccuracies have arisen from the extensive milling or grinding.

In accordance with conventional dental techniques, a dental practitioner makes certain dental prostheses or appliances in the dental office, sometimes while the patient is waiting. Such prostheses or appliances include dental inlays such as fillings. Owing to the limitations inherent in conventional dental office facilities, the fillings produced by the dental practitioner are invariably made of amalgam or other material which has a limited strength.

OBJECTS OF THE INVENTION

An object of the present invention is to provide an improved method for producing dental prostheses and restorations, including fillings, crowns, bridges and splints.

Another object of the present invention is to provide such a method which is more ecomomical and efficient than conventional techniques.

Another, more particular, object of the present invention is to provide such a method which reduces the labor required.

Another particular object of the present invention is to provide such a method which reduces or substantially eliminates waste of precious metals.

A further particular object of the present invention is to provide a method wherein the production of several dental prostheses or restorations for different patients is facilitated by producing a common blank approximating the shapes of the several prostheses.

Yet another object of the present invention is to provide such a method which reduces the costs of producing prosthetic dental appliances, including fillings, crowns, bridges, etc.

An additional particular object of the present invention is to provide such a method which produces improved dental prostheses and restorations and, more particularly, dental prostheses and restorations which are stronger, of a closer and more accurate fit, more durable and less prone to failure than conventional prosthetic dental devices.

Yet another object of the present invention is to provide a system for essentially automatically preparing prosthetic dental implants, restorations, splints, fixed bridges, crowns or inlays/overlays.

A further object of the present invention is to provide a mold assembly useful in producing prosthetic dental appliances.

Yet another object of the present invention is to provide a kit which will facilitate the production of dental prostheses and restorations including fillings, crowns, bridges, splints, etc.

SUMMARY OF THE INVENTION

A system for use in preparing a dental prosthesis comprises, in accordance with the present invention, a signal generator for generating an electrical signal encoding geometric specifications of a dental prosthesis, the specifications including dimensions and shape of a tooth preparation at a dental site at which the prosthesis is to be affixed and configuration of the prosthesis. The system further comprises a robot mechanism for placing a first mold component and a second mold component, selected in accordance with the electrical signal, in predetermined relative positions to form a mold cavity, the first mold component corresponding in shape and dimensions to the tooth preparation. The system also comprises a filling device, a furnace and a computer. The filling device serves to introduce into the mold cavity a quantity of a fluidic solidifiable dental material such as a liquid or liquifiable precious metal or alloy or composite material. The metal or alloy may be in any of a number of equivalent forms, for example, powder, pellets or ingots. The robot mechanism and the filling device are at least partially disposed inside the furnace. The computer is operatively connected to the robot mechanism and the filling device for controlling and sequencing the operation thereof.

Pursuant to another feature of the present invention, a milling device or other mechanism is operatively connected to the computer for selectively removing material, in response to signals from the computer, from at least one of the mold components prior to placement of the second mold component into juxtaposition to the first mold component.

Pursuant to another feature of the present invention, the computer includes means for calculating the quantity of the fluidic solidifiable dental material to be introduced into the mold cavity defined by the mold components. In addition, a sensor is advantageously provided for measuring the fluidic solidifiable dental material. The sensor may include, for example, a flow rate measuring device, a weight measuring device or a pellet counter.

The mold components used in a system in accordance with the present invention are generally made of refractory material.

The instant invention offers the great advantage of allowing milling operations to be performed on refractory materials. Refractory materials are substantially softer and thus easier to machine than the dental materials (gold, alloy, composite) which are presently machined in accordance with CAD/CAM techniques.

A dental kit comprises, in accordance with the present invention, a plurality of preformed first mold components corresponding to respective preselected tooth preparations, and a plurality of preformed second mold components corresponding to respective ones of the first mold components and to respective tooth restoration surfaces. As mentioend hereinabove, the mold components are preferably made of refractory materials and represent preselected nearest net shapes.

Such a dental kit in accordance with the present invention also advantageously incldues a plurality of fluidic solidifiable dental materials. The dental materials are used in casting dental shapes such as fillings and the supporting super-structures of crowns, bridges and splints. The provision of dental materials separately facilitates the production of dental prostheses which match the color of the patient's teeth.

A method for facilitating the making of a dental restoration comprises the steps of providing the aforedescribed kit and generating an electrical signal encoding geometric specifications of a dental prosthesis, the specifications including dimensions and shape of a tooth preparation at a dental site at which the prosthesis is to be affixed and configuration of the prosthesis. In another step, one of the first mold components and one of the second mold components are selected in accordance with the geometric specifications contained in the electrical signal. Then, a quantity of a fluidic solidifiable dental material is introduced into at least one of the selected first mold component and the selected second mold component. The selected first mold component and the selected second mold component are juxtaposed to thereby form a mold cavity corresponding to the dental prosthesis. The solidifiable dental material is preferably introduced into one of the selected mold components prior to the juxtaposition thereof. However, it is within the contemplation of the invention that the introduction of the dental material may be implemented subsequently to the juxtaposition of the selected mold components.

Pursuant to another feature of the present invention, the method further comprises the steps of (a) heating the selected mold components and the quantity of the fluidic solidifiable dental material, and (b) maintaining the mold components in juxtaposition to one another during the step of heating.

In another step, in accordance with the present invention, the amount of the quantity of the fluidic solidifiable dental material is automatically calculated prior to the step of introducing.

It is also within the contemplation of the invention that the selected mold components will require some machining prior to formation of the mold cavity and the introduction of the fluidic solidifiable dental material. The mold components are made of refractory material to enable proper execution of the heating step. In addition, as noted above, refractory material is softer than solid dental materials and is thus easier to machine. However, it is to be noted that the dental prosthesis formed upon the completion of the heating step may be machined, if necessary, to conform the dental form exactly to the dentists specifications.

In accordance with the present invention, where the dental prosthesis or restoration is prepared completely in the dentist's office, at least one of the mold components may be machined in tandem with the drilling of a patient's tooth or teeth by a dentist to prepare the teeth for the reception of the prosthesis. As described below, the machining may be performed by a milling device connected in a pantograph type arrangement to a dentist's drill. In that way, the mold component corresponding to a prepared tooth is milled simultaneously with the preparation. Alternatively, as described below, electrically encoded three-dimensional surface data may be loaded into a computer during or before the tooth preparation procedure. That electrically encoded data is then utilized by the computer to control milling operations. It is to be understood, of course, that the machining of the mold components in accordance with the present invention may be performed by cutting devices other than milling machines, for example, lasers and ultrasonic devices.

A method for use in preparing dental appliances comprises, in accordance with the present invention, the steps of (a) receiving a plurality of electrical signals encoding geometric specifications of a plurality of dental prostheses, the specifications including dimensions and shape of tooth preparations at dental sites at which the prostheses are to be affixed and configuration of the prostheses, and (b) calculating from the geometric specifications additional geometric specifications of a common nearest net shape from which all of the plurality of dental prostheses may be machined. Upon completion of the step of calculating, a pair of mold components is provided to produce, in cooperation with one another, a mold cavity having dimensions and configuration corresponding at least substantially to dimensions and configuration of the common nearest net shape. The mold components are placed in predetermined relative positions to form the mold cavity, a quantity of a fluidic solidifiable dental material is introduced into the mold cavity, and a prosthesis form is subsequently removed from the mold cavity upon solidification of the dental material with which the mold cavity is filled.

Another method for use in preparing a dental prosthesis comprises, in accordance with the present invention, the steps of (a) generating an electrical signal encoding geometric specifications of the prosthesis, the specifications including dimensions and shape of a tooth preparation at a dental site at which the prosthesis is to be affixed and configuration of the prosthesis, and (b) in response to the electrical signal, providing a first mold component having a surface at least approximately conforming to the tooth preparation and a second mold component to produce, in cooperation with the first mold component, a mold cavity having dimensions and configuration corresponding at least substantially to dimensions and configuration of the prosthesis. In further steps (c) and (d), the mold components are placed in predetermined relative positions to form the mold cavity, and a quantity of a fluidic solidifiable dental material is introduced ionto the mold cavity so formed. The mold components and the quantity of a fluidic solidifiable dental material are then heated while maintaining the mold components in juxtaposition with one another.

Pursuant to another feature of the present invention, the prosthesis form is shipped to a user for machining of the prosthesis form by the user. Preferably, an electronic codification of the dimensions and configuration of the prosthesis form is conveyed to the user together with the prosthesis form.

Pursuant to yet another step of a method of the present invention, the prosthesis form is attached to a support having markers for providing a distance reference for the prosthesis form, the support being shipped to the user with the prosthesis form. In addition, the support is provided with alignment elements for guiding the support molded form into a predetermined relationship with a machining apparatus.

A mold assembly for use in preparing a dental prosthesis comprises, in accordance with the present invention, a mold component having a surface at least approximately conforming to a tooth preparation, a support attached to the mold component, markers on the support for providing a distance reference for the mold component, and alignment elements on the support for aligning and guiding the mold component into a predetermined relationship with another mold component to form a mold cavity.

Another assembly for use in preparing a dental prosthesis comprises, in accordance with the present invention, a molded form having a surface at least approximately conforming to a tooth preparation for a particular patient, the molded form constituting a preform for a dental prosthesis for the particular patient, a support, the molded form being removably attached to the support, and markers on the support for providing a distance reference for the molded form.

BRIEF DESCRIPTION OF THE DRAWING

FIG. 8 is an elevational view of a distal end of the embodiment of FIG. 7, taken in the direction of arrow VIII.

FIG. 9 is a plan view of a reference stylus usable in conjunction with the data generating device of FIGS. 3 and 7.

FIG. 10 is a plan view of another reference stylus usable in conjunction with the data generating device of FIGS. 3 and 7.

FIG. 11 is a partially diagrammatic perspective view of an embodiment of a contour data generating device shown in FIG. 1.

FIG. 12 is a partial perspective view, on an enlarged scale, of the contour generating device of FIG. 11, showing its use with a dental patient.

FIG. 13 is a partial perspective view, on an even larger scale, of another embodiment of the contour generating device of FIG. 1, showing its use with a dental patient.

FIG. 14 is perspective view of another contour data generating device usable in a dentistry system.

DETAILED DESCRIPTION

Figure 1:
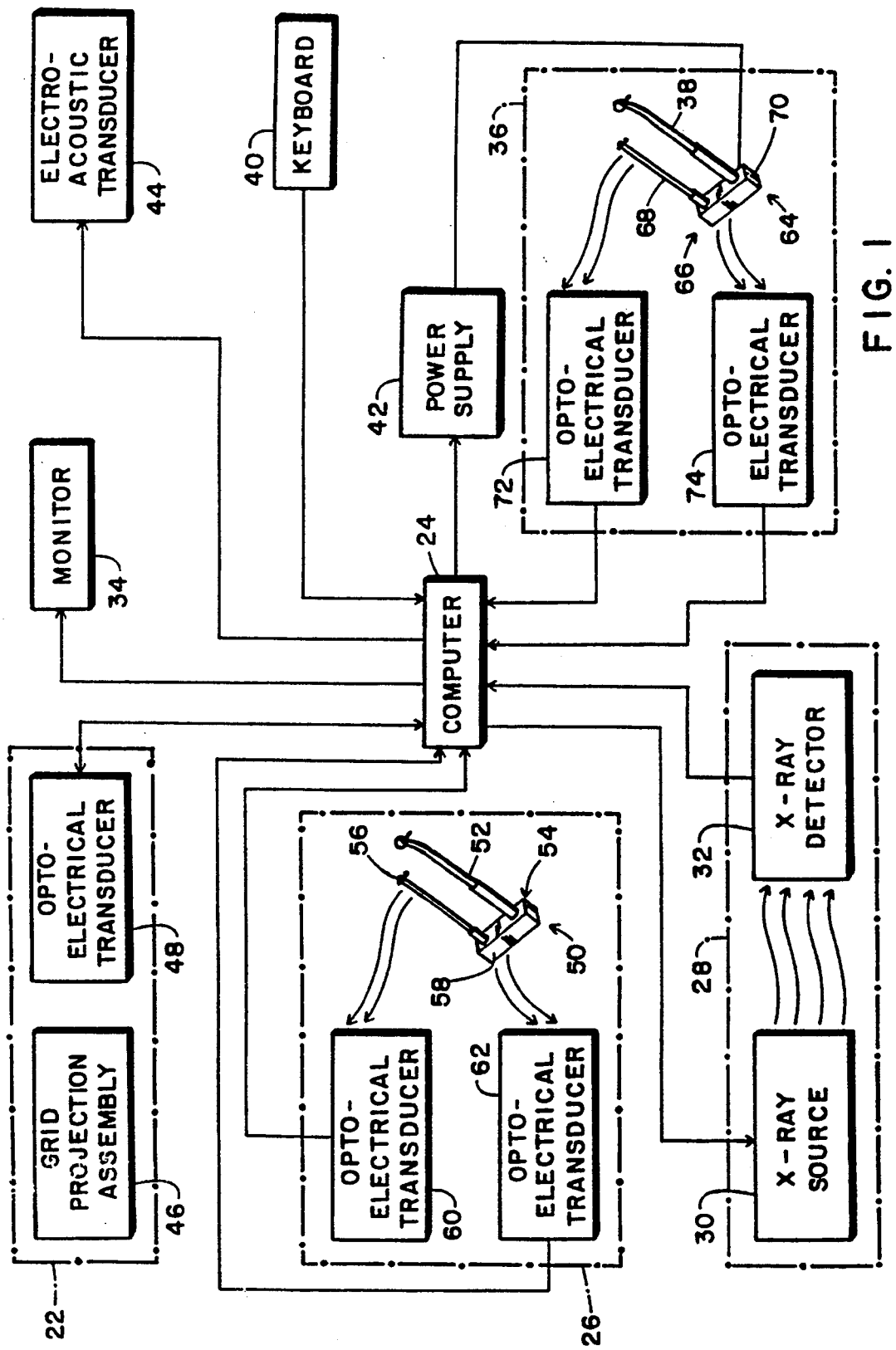
FIG. 1 is a block diagram of a system effecting a desired modification in the shape of a pre-existing object such as a tooth to which access is restricted.

As illustrated in FIG. 1, a computerized interactive system for producing a modification in the shape of an object such as a tooth to which access is limited comprises a first data generating device or assembly 22 for providing a computer 24 with electrically encoded data, specifically, digitized video signals representing a three-dimensional surface of an object such as a tooth. A second data generating device or assembly 26 is operatively connected to computer 24 for transmitting thereto digitized video signals containing information pertaining to a curvilinear contour on the surface of the three-dimensional surface of the tooth. In addition, computer 24 may receive from a third data generating device or assembly 28 digitized input signals relating to internal structures of the tooth being scanned. Specifically, data generating device 28 may take the form of an X-ray device such as used in current intra-oral radiology or other methodologies and basically comprises a source 30 of X-ray radiation and a detector 32 for receiving the X-ray radiation after it passes through a tooth and converting the incident radiation into a digital data stream fed to computer 24.

As further illustrated in FIG. 1, the computerized interactive dentistry system also comprises a display device 34 such as a monitor or holographic projector. In response to data signals, computer 24 generates a three-dimensional view on display of monitor 34 of the tooth or teeth under examination. More specifically, computer 24 is provided with any commercially available stereophotogrammetric triangulation program for calculating and displaying, on the basis of the video input signals from data generating devices 22, 26 and 28, three dimensional surfaces and contours of the tooth or teeth.

The computerized interactive dentistry system of FIG. 1 further includes another data generating device or assembly 36 which provides computer 24 with digitized video information as to the location of the operative tip of a cutting instrument 38 such as a dentist's drill relative to the three-dimensional structural features of the tooth. Data generating device 36 thus enables computer 24 to monitor modifications to the shape of the tooth as those modification are being made in the tooth.

The system of FIG. 1 is further provided with any of several instruction input devices such as a keyboard 40, a mouse (not shown), or a contact sensitive surface of monitor 34, whereby an operator such as a dentist or dental technician may instruct the computer to display a desired tooth preparation on monitor 34. In addition, or alternatively, computer 24 may use input from drill data generating device 36 as instructions regarding, for example, the depth of a tooth preparation to be displayed on monitor 34.

Upon selecting a desired tooth preparation illustrated on monitor 34, the dentist operates drill 38 to cut a recess into the tooth (in the case of a filling or inlay) or or to remove an outer layer of the tooth (in the case of preparing a form/shape for a crown or other prosthetic restoration). Computer 24 monitors the location of the operating tip of the drill via data generating device 36 and, if the drill approaches a boundary previously defined to the computer during an interactive tooth preparation selection operation, either interrupts the power provided to the drill via a supply 42 or alerts the dentist via a signaling device such as an electro-acoustic transducer 44.

As depicted schematically in FIG. 1 and discussed in greater detail hereinafter, data generating device 22 includes a grid projection assembly 46 for optically imposing a grid onto the surface of the patient's tooth. Data generating device 22 also includes an opto-electrical transducer 48 such as a charge-coupled device for optically sensing or scanning the tooth surface onto which the grid is projected by assembly 46. It is to be understood that the grid pattern projected on the tooth surface need not be an orthogonal grid having two sets of lines at right angles to one another, but may instead have the two sets of lines oriented at an acute angle. Moreover, although the dental scanning systems described herein preferably incorporate an optical grid, it is to be appreciated that a grid may be imposed onto the tooth surface by other methods, such as adhesively attaching to the tooth surface a transparency provided with a grid. In addition, the grid provided on such a transparency need not take the specific form of two sets of orthogonal lines but may instead take the form of an array of virtually any shapes, such as dots or circles. It is only necessary that the precise size of the shapes be known and programmed into the computer.

As further depicted in FIG. 1 and described in detail hereinafter, data generating device 26 comprises a pantograph-type component 50 which incorporates a stylus member 52 and a pantograph extension 54 in turn including a pantograph arm 56 and a bridge element 58. Bridge element 58 connects pantograph arm 56 to stylus member 52. Data generating device 26 further comprises at least a pair of opto-electrical transducers 60 and 62 preferably in the form of respective charge-coupled devices ("CCD"s). Pantograph component 50 enables computer 24 to track, from outside the mouth, the motions of the tip of the stylus member inside the mouth and even beneath the gum line.

Accordingly, data generating devices 22, 26 and 28 provide to computer 22 electrically encoded data completely defining the structure of the tooth on which a dentist is working. Computer 24 then "draws" the tooth on monitor 34. At that juncture the dentist instructs the computer to modify the displayed three-dimensional shape. For example, the dentist may use keyboard 40 to input a command that a predefined tooth preparation, in graphic form, be overlaid on the three-dimensional graphic representation of the tooth. The size of the tooth preparation relative to the tooth may be specified by entering a depth dimension via keyboard 40, data generating device 36, a mouse or a contact-sensitive surface of monitor 34. Alternatively, computer 24 may be programmed to automatically select a possible tooth preparation in accordance with the data from data generating devices 22, 26 and 28. In accordance with yet another alternative procedure, the dentist may command the computer to alter the graphic representation of the tooth, for example, by removing a layer of several millimeters from a surface selected by the dentist or by removing a selected volume of tooth from all five surfaces above the gum line to a contour below the gum line defined by the second data generating device 26.

As further depicted in FIG. 1 and described in detail hereinafter, data generating device 36 comprises a pantograph-type component 64 which incorporates drill 38 and a pantograph extension 66 in turn including a pantograph arm 68 and a bridge element 70. Bridge element 70 connects pantograph arm 68 to drill 38. Data generating device 36 further comprises at least a pair of opto-electrical transducers 72 and 74 preferably in the form of respective charge-coupled devices ("CCD"s). Pantograph component 64 enables computer 24 to track, from outside the mouth, the motions of the tip of drill 38 inside the mouth and even inside a tooth.

In a preferred form of the system described herein, data generating device 36 is the same as data generating device 26 with stylus element 52 replaced by drill 38. Moreover, upon the selection of a desired tooth preparation via computer 24, monitor 34 and an instruction input device such as keyboard 40, drill 38 is used by the dentist to provide the displayed tooth preparation in the subject tooth. Computer 24 monitors the output signals of opto-electrical transducers 72 and 74 thereby tracks the cutting motions of the operating tip of drill 38 inside the subject tooth. The excavations into the tooth are displayed in real time on monitor 34 by computer 24.

Figure 2:
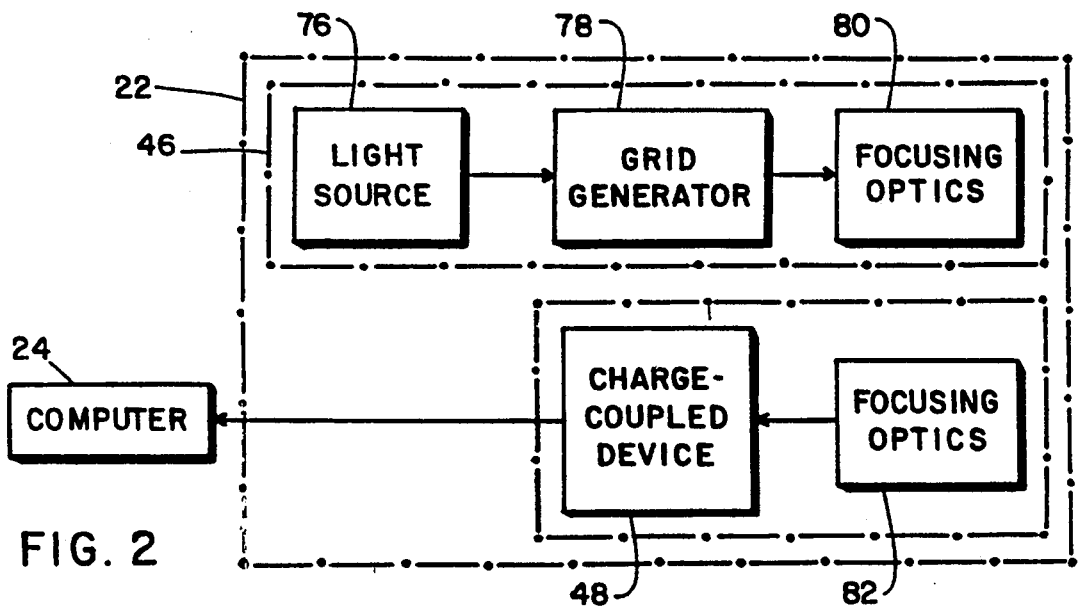
FIG. 2 is a block diagram showing details of a surface data generating device shown in FIG. 1.

As shown in FIG. 2, grid projection assembly 46 of data generating device 22 includes a light source 76, a grid generator 78 and an assembly 80 of light guides and lenses for guiding the grid light along a path through the data generating device and for focusing the grid light on the surface of a subject tooth. The light subsequently reflected from the tooth surface is gathered by further optical elements 82 and focused by those elements on the light sensitive sensor surface of charge-coupled device ("CCD") 48. In response to a sensed pattern of light intensities, CCD 48 generates and transmits to computer 24 a digitized video signal containing information used by computer 24 to calculate the dimensions of the subject tooth and to display the tooth's structure in a three-dimensional graphic representation on monitor 34.

Figure 3:
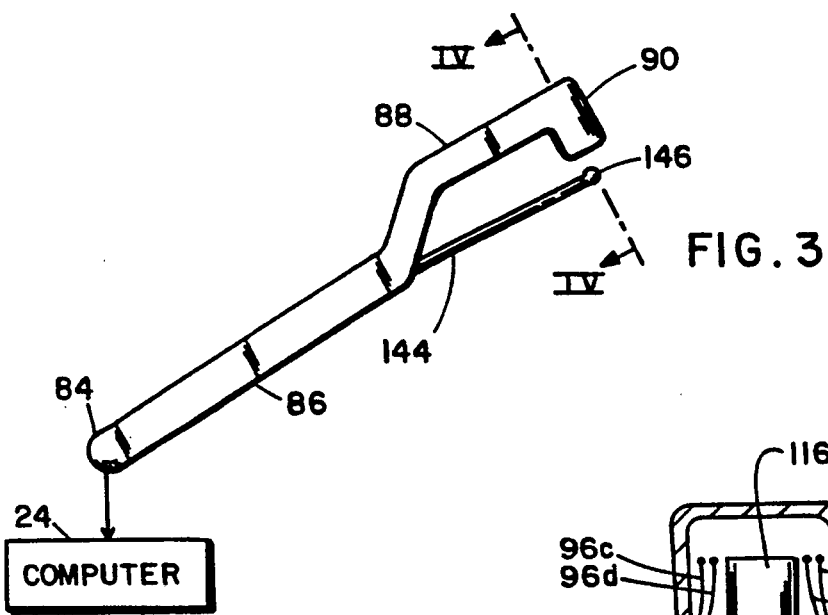
FIG. 3 is partially a block diagram and partially a schematic elevational view of a particular embodiment of the surface data generating device of FIG. 2.

As shown in FIG. 3, the components 76, 78, 80, 82 and 48 of data generating device 22 may be housed in an elongate instrument frame or holder 84 including a handle 86 and a stem portion 88 displaced laterally with respect to a longitudinal axis of handle 86.

Figure 4:
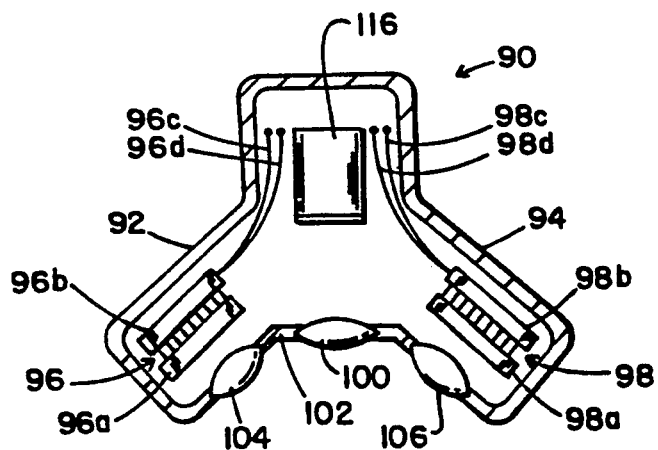
FIG. 4 is a cross-sectional view taken along line IV—IV in FIG. 3.

In a preferred form of the grid projection instrument, illustrated in detail in FIG. 4, holder 84 of FIG. 3 further includes a Y-shaped distal end portion 90 having a pair of hollow legs 92 and 94 housing respective CCDs 96 and 98. Each CCD includes a respective photosensitive sensor array 96a and 98b and respective sequencing and processing electronics 96b and 98b. The sequencing and processing electronics 96b and 98b have input and output leads 96c, 96d and 98c, 98d extending to computer 24 through stem portion 88.

Light containing a grid pattern is projected from Y-shaped distal end portion 90 through a focusing lens 100 mounted in a wall 102 between legs 92 and 94. The light subsequently reflected from a subject tooth is focused on sensor arrays 96a and 98a by a pair of lenses 104 and 106 disposed in legs 92 and 94. Lenses 104 and 106 may be considered parts of focusing optics 82 (FIG. 2), while lens 100 is part of focusing optics assembly 80.

Figure 5:
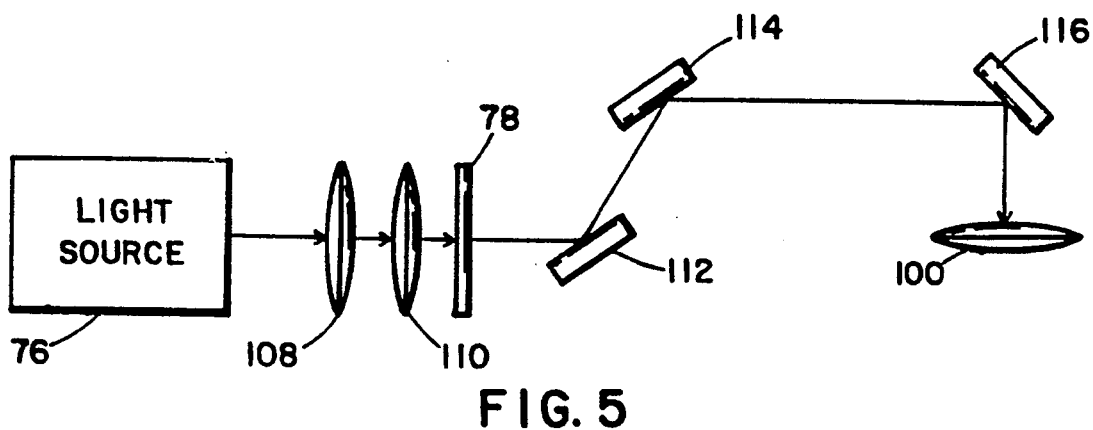
FIG. 5 is a detailed schematic diagram of optical components in a grid projection assembly included in the surface data generating device of FIG. 3.

As shown in detail in FIG. 5, grid projection assembly 46 includes light source 76 (also shown in FIG. 2), a pair of collimating lenses 108 and 110, grid generator 78 (see FIG. 2) in the form of a plate provided with a grid pattern, and three mirrors or prisms 112, 114, 116 for directing the grid-containing light rays through stem portion 88 (FIG. 3) to lens 100. Of course, frame or holder 84 may be provided with various movable mounting elements (not shown) for adjusting the focuses of the various lenses.

Figure 6:
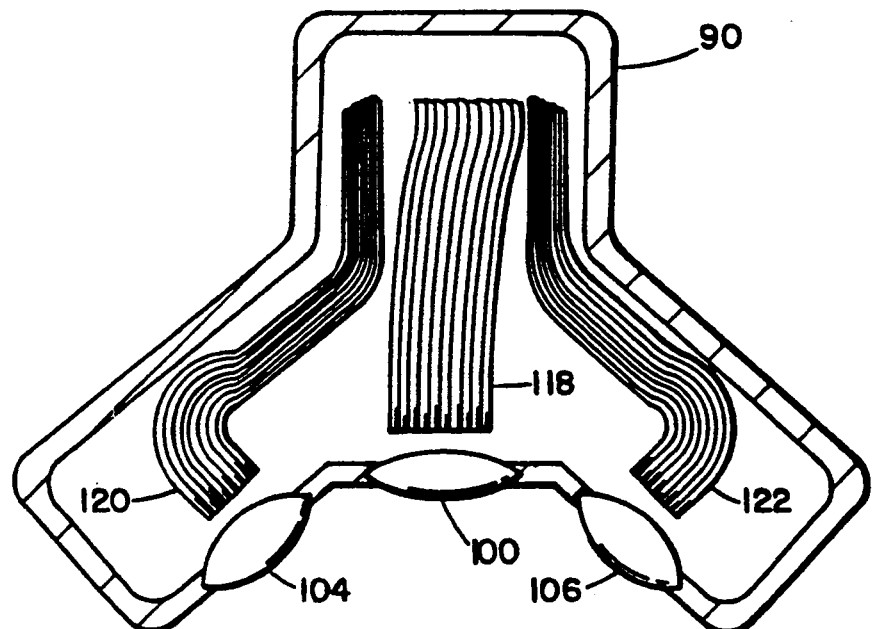
FIG. 6 is a cross-sectional view, similar to FIG. 4, of another particular embodiment of the surface data generating device of FIG. 2.

The grid light may be guided through the grid projection instrument or frame 84 by elements other than those illustrated in FIG. 5. As depicted in FIG. 6, an output array of light beams is guided to lens 100 by a bundle 118 of optical fibers, while a pair of optical fiber input bundles 120 and 122 receive incoming optical radiation focused on the input ends of bundles by lenses 104 and 108.

Fiber bundles 120 and 122 guide the incoming radiation to a pair of CCDs (not shown) disposed in instrument frame 90 at a more proximal end of the frame, for example, in the handle. Rather than two separate CCDs, the first data generating device 22 may include a single CCD (not shown) disposed in the handle 84 (FIG. 3) and means for directing light from two separate optical pathways to the CCD.

Figure 7:
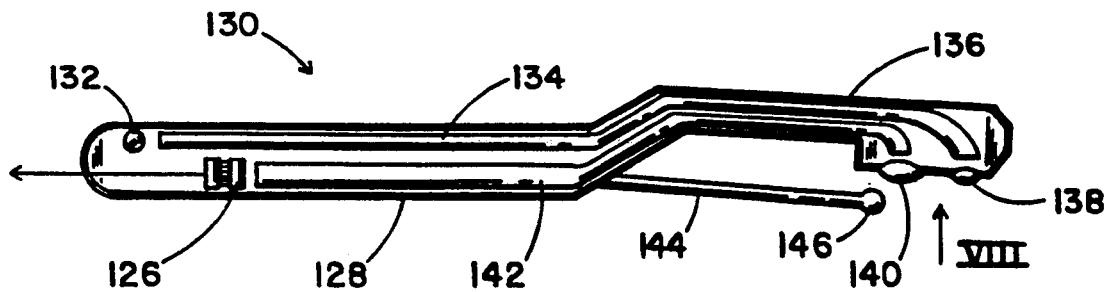
FIG. 7 is a schematic cross-sectional longitudinal view of yet another particular embodiment of the surface data generating device of FIG. 2.

As schematically shown in FIGS. 7 and 8, a data generating device or optical probe 124 may incorporate a single CCD transducer 126 disposed in a handle 128 of an elongate instrument frame or casing 130. The handle 128 also houses a grid source 132. An optical fiber bundle 134 guides a grid pattern from grid source 132 through a part of handle 128 and a stem portion 136 of frame 130 to a distal end of the probe. At the distal end, the grid pattern is focused by a lens 138 onto a subject tooth, the reflected radiation pattern being focused by another lens 140 onto the distal or input end of another fiber optic bundle 142 extending to CCD 126.

As shown in FIGS. 3 and 7, frame member 84 and optical probe frame 130 are provided with a stylus element 144 having an enlargement 146 at its distal end. Enlargement 146 is disposable in the visual field of the respective optical scanning element or elements, whether CCD 48, CCDs 96 and 98, or CCD 126, for providing computer 24 with a reference distance or dimension at the surface of a subject tooth being scanned. Computer 24 is thereby able to calculate absolute values for the dimensions of various surface features. Computer 24 measures distances by calculating the number of pixels in the respective sensor array (e.g., 96a and 98a) which cover a feature whose dimensions are being determined. Inasmuch as computer 24 is preloaded with the actual dimensions of enlargement 146, the computer is able to compute actual distances by comparing the number of pixels corresponding to enlargement 146 with the number of pixels corresponding to the features of the tooth.

Stylus element 144 is retractable into handle 86 or 128. Retraction may be implemented either manually or automatically, for example, by a small motor and rack and pinion (not illustrated) inside the respective handle. Moreover, stylus 144 is advantageously replaceable by other elements such as stylus 148 shown in FIG. 9 or stylus 150 shown in FIG. 10.

Stylus 148 is formed at a distal end with three prongs 152, 154 and 156 each having a respective sphere 158, 160 and 162 at its free end. Spheres 158, 160 and 162 may have different sizes for facilitating the measurement of anatomical distances by computer 24. Similarly, stylus 150 has a plurality of prongs 164, 166, 168, 170 and 172 each provided at its free end with an enlarged formation 174, 176, 178, 180 and 182 of a respective geometric shape and a respective transverse dimension.

In using a data generating device equipped with stylus 148, a dentist places at least two of spheres 158, 160 and 162 on the surface of the tooth. Similarly, two enlarged end formations 174, 176, 178, 180 and 182 are positioned in engagement with a tooth surface during use of a data generating device incorporating stylus 150.

As depicted in FIGS. 11 and 12, contour data generating device 26 (FIG. 1) comprises three CCD cameras 184, 186 and 188 fixed to the free ends of respective adjustable mounting arms 90, 192 and 194 in turn connected at their other ends to a pedestal member 196. Contour data generating device 26 further comprises three transparent plates 198, 200 and 202 each provided with a respective grid 204 (only one designated in the drawing) and secured to a common substantially L-shaped support arm 206. Support arm 206 is cemented or otherwise attached to the jaw of a patient P prior to the use of the contour data generating device.

It is to be noted that although plates 198, 200 and 202 are illustrated as being orthogonally disposed and as having Cartesian orthogonal grids, it is not necessary for effective calculation of distances and angles that the plates and grids be so oriented. An ordinary modification of the stereophotogram-metric triangulation program is all that is required for the system of FIG. 1 to function with plates 198, 200 and 202 and/or the grid lines thereof oriented at acute angles.

Any two CCD cameras 184, 186 and 188 correspond to opto-electrical transducers 60 and 62 of FIG. 1. Although three CCD cameras are preferred, in some instances two may be sufficient.

As further illustrated in FIGS. 11 and 12, contour data generating device 26 includes pantograph-type component 50. As described hereinabove with reference to FIG. 1 (includes essentially a mirror image of illustrations in FIG. 11 and 12), pantograph component 50 incorporates stylus member 52, pantograph arm 56 and bridge element 58. CCD Cameras 184, 186 and 188 enable computer 24 to track orthogonal components of the motion of a predetermined point 208 on pantograph arm 56 against respective reference frame plates 198, 200 and 200, respectively. Because pantograph arm 56 is fixed with respect to stylus member 52, computer 24 is accordingly able to track, from outside the mouth of patient P, the motions of the tip of the stylus member 52 inside the mouth and even beneath the gum line.

Pantograph component 50 is mounted to the free end of a linkage 210 including a plurality of pivotably interconnected arm members 212. The base of linkage 210, like pedestal member 196 is secured to a base 214.

Both stylus member 52 and pantograph arm 56 are rotatably secured to bridge element 58 so that they can rotate about respective longitudinal axes. Pantograph arm 56 is coupled to stylus member 52 via an endless toothed belt 53 whereby rotation of stylus arm 52 about its longitudinal axis by an operator results in a simultaneous rotary motion of pantograph arm 56.

Accordingly, stylus member 52 is free to be moved by an operator along three translational axes and three rotational axes, the resulting motion being duplicated by pantograph arm 56.

An alternative way for providing computer 24 with a reference frame against which to measure motions of pantograph arm 56 and concomitantly stylus member 52 is illustrated in FIG. 13. In the specific embodiment shown in FIG. 13, three CCD cameras 216, 218 and 220 are fastened to support member 206 in turn cementable, as discussed above, to the patient's jaw in which the subject tooth is rooted. Pursuant to this embodiment of the contour data generating device, no reference grids are necessary for computer 24 to monitor, via cameras 216, 218 and 220, the motion of pantograph arm 56 and thus stylus member 52.

It is to be noted that the camera assembly of FIG. 13 essentially includes three pixel arrays (not visible in the drawing) disposed in separate reference planes of a three dimensional coordinate system, with the casings of the cameras serving in part to hold three lenses (not designated with reference numerals) at pre-established distances with respect to the respective pixel arrays to focus the light from the tip 208 of the pantograph arm on the pixel arrays. The tip 208 of pantograph arm 56 may be provided with an LED or other marker element to facilitate detection by the optical scanning assembly comprising cameras 216, 218 and 220.

As illustrated in FIG. 14, contour data may be generated by an alternative technique employing a multiple segment support arm 710 which extends from a fixed platform 712. Support arm 710 includes segments 714, 716, 718, 720, 722 and 724 of which the first segment 714 is connected to platform 712. Segments 714–724 are pivotably connected to one another via six rotating joints 726, 728, 730, 732, 734 and 736. By incorporating six separate junctions for rotational movement, an operating instrument (e.g., drill) 738 connected to the free end of a last or outermost arm 724 can move with six degrees of freedom, specifically along three translational axes and three rotational axes.

Stationary platform 712 and segment 714 are connected at joint 726 to provide rotation relative to one another about a substantially vertical axis. First segment 714 and second segment 716 are coupled to one another for rotation about an axis which is essentially a horizontal axis and which axis is coextensive with the axes of segments 714 and 716. Joint 728 provides this rotational movement. Similarly, arm segments 716 and 718 are rotatably linked via joint 730.

A probe or pantograph-type extension 744 is mounted to the outermost segment 724 and through a belt 746 rotates in synchronism with operating instrument 738. In this fashion, probe 744 is slaved to operating instrument 738. Accordingly, a three-dimensional configuration or contour traced by the tip of operating instrument 738 will be replicated by a tip of pantograph extension 744.

Each joint 726–736 is formed to have sufficient friction to allow the joint to hold a position once placed therein. However, the friction of each joint is low enough so that movement of the joint can be commenced fairly easily.

A plurality of digital encoders 740 are mounted to arm segments 714–724. Upon a movement of operating instrument 738, encoders 740 transmit to computer 24 respective signals encoding the amount of motion in the various six degrees of freedom. The monitoring device of FIG. 14 need not include pantograph extension 744 since motion tracking is accomplished via the encoder output signals rather than optically.

Upon the transmission to computer 24 of sufficient data from surface data generating device 22 and contour data generating device 26 (FIG. 1), computer displays partial or complete graphic representations on monitor 34 of the subject tooth or teeth. The graphic representations include the visible three-dimensional surfaces of each such tooth, as well as invisible base line data fed to computer 24 by contour data generating device 26. In addition, computer 24 may be provided with electrically encoded data specifying internal structures such as the dentine inside each tooth and prior fillings or other prosthetic devices.

Upon viewing a tooth on monitor 34, a dentist may select a preparation which may be appropriate for the particular condition of the tooth. As described above, this selection may be accomplished via an instruction corresponding to an electrically encoded tooth preparation previously loaded into the memory of computer 24. Alternatively, the selection may be implemented by inputting dimensional parameters via keyboard 40, including distances, angles, planes and percentages. As another alternative, computer 24 may provide a menu selection on monitor 34, selections being made from the menu via the keyboard, a mouse or a touch-sensitive monitor screen. In yet another alternative procedure, computer 24 may be programmed to recognize structural features of the tooth, such as its type, the location and shapes of cavities and prior inlays or onlays and to automatically select a possible preparation in accordance with the recognized features. The computer may be further programmed to vary the size of the preparation to correspond to the particular tooth. The dentist would then view the selected preparation and alter it on screen by any of the above-described instruction input techniques. Upon arriving at a final, desired preparation, the dentist will inform computer via keyboard 40.

As discussed hereinabove, drill 38 (FIG. 1) is then used to remove a portion of the subject tooth. Computer 24 may control the supply of power to the drill so that the drill is operational only within the regions selected for removal during the interactive stage of the dental process. Accordingly, drill 38 will be de-energized until the cutting tip of the drill is in near engagement with a surface to be cut. Then computer 24 enables the transmission of power from supply 42 to drill 38. Upon the subsequent approach of the cutting tip of the drill to a defined boundary, as sensed preferably via data generating device 46 (FIG. 1), i.e., via CCD cameras 184, 186, 188 or 216, 218, 220 monitoring a pantograph component 50, computer 24 automatically interrupts power transmission from supply 42 to drill 38.

Figure 15:
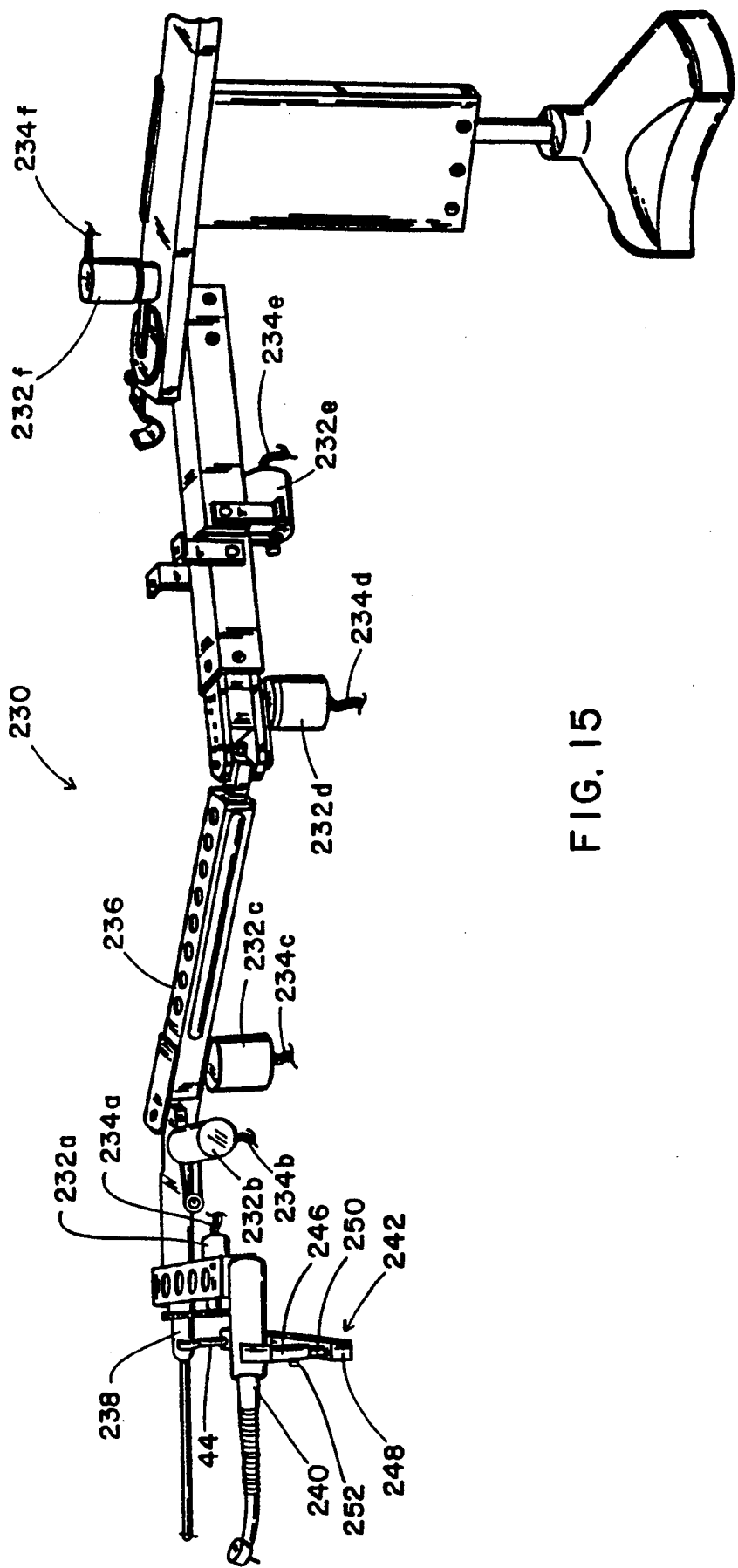
FIG. 15 is a perspective view of drill movement control assembly.

FIG. 15 illustrates a drill movement control assembly 230 similar in geometric design to the linkage 226 of FIG. 14. However, the encoders 22 of that linkage mechanism have been replaced in the movement control assembly of FIG. 15 with motors 232a–232f connected via respective energization leads 234a–234f to computer 24 (FIG. 1). In addition, in drill movement control assembly 230, the free end of a linkage 236 is connected to a pantograph arm 238 rather than to a drill member 240. Drill member 240 is rigidly but removably coupled to pantograph arm 238 via a U-shaped bridge 242 including a pair of legs 244 and 246 fastened to pantograph arm 238 and drill 240, respectively, and a transverse connector piece 248. Yet another leg member 250 is rigid with connector piece 248 and is telescopingly received inside leg 246. A spring loaded release latch 252 serves to removably clamp leg member 250 inside leg 246. Release latch 252 constitutes a safety mechanism enabling a dentist to remove drill 240 from a patient's mouth if the motion of the drill therein in response to operation of motors 232a–232f by computer 24 is not satisfactory to the dentist.

Upon the selection of a desired or optimum tooth preparation by a dentist and a subsequent signal for commencing tooth cutting, computer 24 generates a series of signals selectively energizing motors 232a–232f to move the operative end of drill 240 into engagement with those regions of the subject tooth which are to be removed to achieve the desired preparation. As described hereinabove, computer 24 controls the energization of drill 240 so that the drill is operative only in preselected zones in and about the regions of tooth to be removed.

Figure 16:
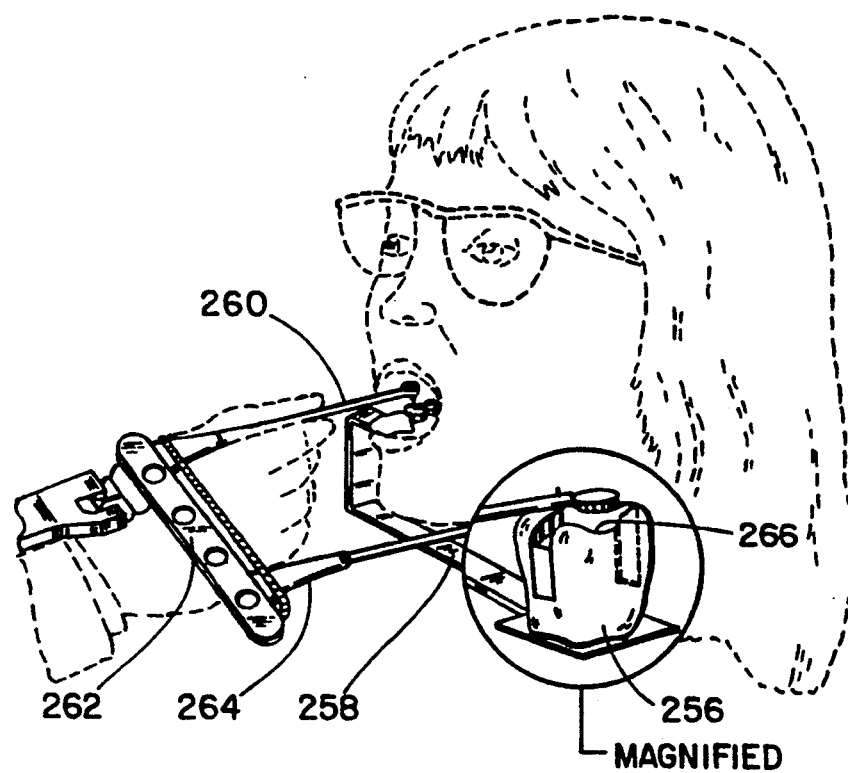
FIG. 16 is a partial perspective view, on an enlarged scale, of a drill movement restriction assembly, showing a tooth preparation preform on an even larger scale.

Limiting the motion of a dentist's drill 254 may be accomplished by selecting a tooth preparation preform 256 from a kit of preforms (see FIG. 16). Preform 256 may be selected by computer 24, as described above, to confrom to a desired preparation or may be manually selected. Preform 256 is cemented to one end of a support bracket 258, the other end of which is attached to the patient's jaw wherein is rooted a tooth to be provided with the preparation of the selected preform. A pantograph assembly including a drill 260, a bridge member 262 and a pantograph arm 264 is then used to cut the tooth. A tip on the pantograph arm corresponding to the cutting tip of drill 260 is inserted into a cavity 266 in preform 256 (in the case of a filling or inlay). Engagement of the tip of pantograph arm 264 with the walls of cavity or recess 266 limits the concomitant motion of the drill, whereby the tooth is provided with a recess having the same geometric structure as recess 266.

Accordingly, a kit is provided of dental preparation preforms in different sizes and shapes. Some preforms correspond to inlays such as that shown in FIG. 16. Other preforms correspond to onlays or crowns. The kit may also include prefabricated prosthetic devices, that is, preformed inlays and onlays for attachment to tooth surfaces upon preparation of those srufaces as described hereinabove.

Computer 24 has a data memory loaded with electrically encoded data corresponding to all of the preformed inlays and onlays in the kit. More specifically, the predefined tooth preparations selectable automatically by computer 24 or in response to instructions received via keyboard 40 or otherwise all correspond to respective prosthetic inserts of several predefined sizes.

Accordingly, computer 24 operates to select a desired tooth preparation and to control the formation of that preparation in the subject tooth. Upon the completion of the preparation, either the computer or the dentist selects the appropriately sized inlay or onlay. If necessary in a particular case, a selected preformed inlay or onlay can be machined prior to attachment to a tooth. Computer 24 may control the machining operations in a conventional numerically controlled operation or may serve to limit the range of cutting motions, as described hereinabove with reference to providing a tooth with the desired preparation.

Figure 17:
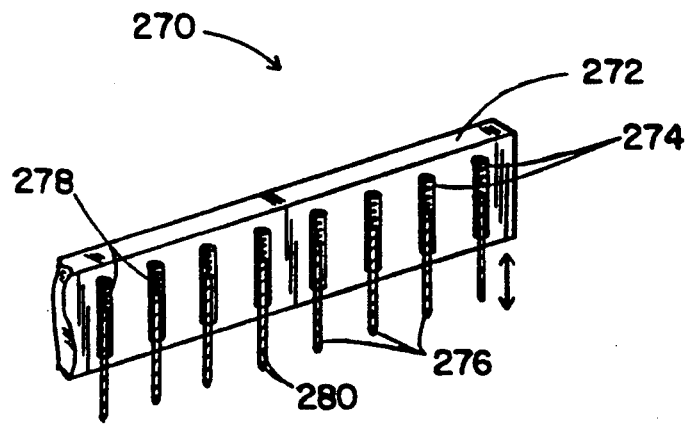
FIG. 17 is a partial schematic perspective view of a reference marker assembly.

FIG. 17 shows an assembly 270 for supplying surface data generating device 22 (FIG. 1) with optically detectable reference distances or displacements at the surface of the object (such as a tooth). Assembly 270 is attachable to the distal end of a dental probe such as instrument frame or holder 84 and comprises a holder member 272 made of transparent material and provided with a linear array of equispaced parallel bores 274 each slidably receiving a respective reference pin or stylus 276. Each stylus is pushed outwardly in a transverse direction relative to holder member 272 by a respective compression spring 278. In addition, each stylus 276 is provided with a series of longitudinally equispaced striations or reference marks 280.

The extensions of styli 276, i.e., the lengths to which the styli are pushed inside holder member 272, are measured by computer 24 through video signals obtained via a pair of optical pathways such as those illustrated in FIGS. 4 and 6. Alternatively, two optical light receiving elements such as prisms (not shown) may be placed on the same lateral side of the stylus array.

In using reference generator assembly 270 of FIG. 17, an operator such as a dentist presses styli 276 against a tooth surface. Under the pressure exerted by the operator, styli 276 are pushed respective distances into bores 274 against the action of springs 278. The displacement of each stylus 276 depends on and is a measure of a height of a respective surface element or zone of the tooth surface.

In most instances only a few (possibly as few as two) different positionings of stylus assembly 270 are required for computer 24 to map the entire surface of the tooth under observation.

Figure 18:
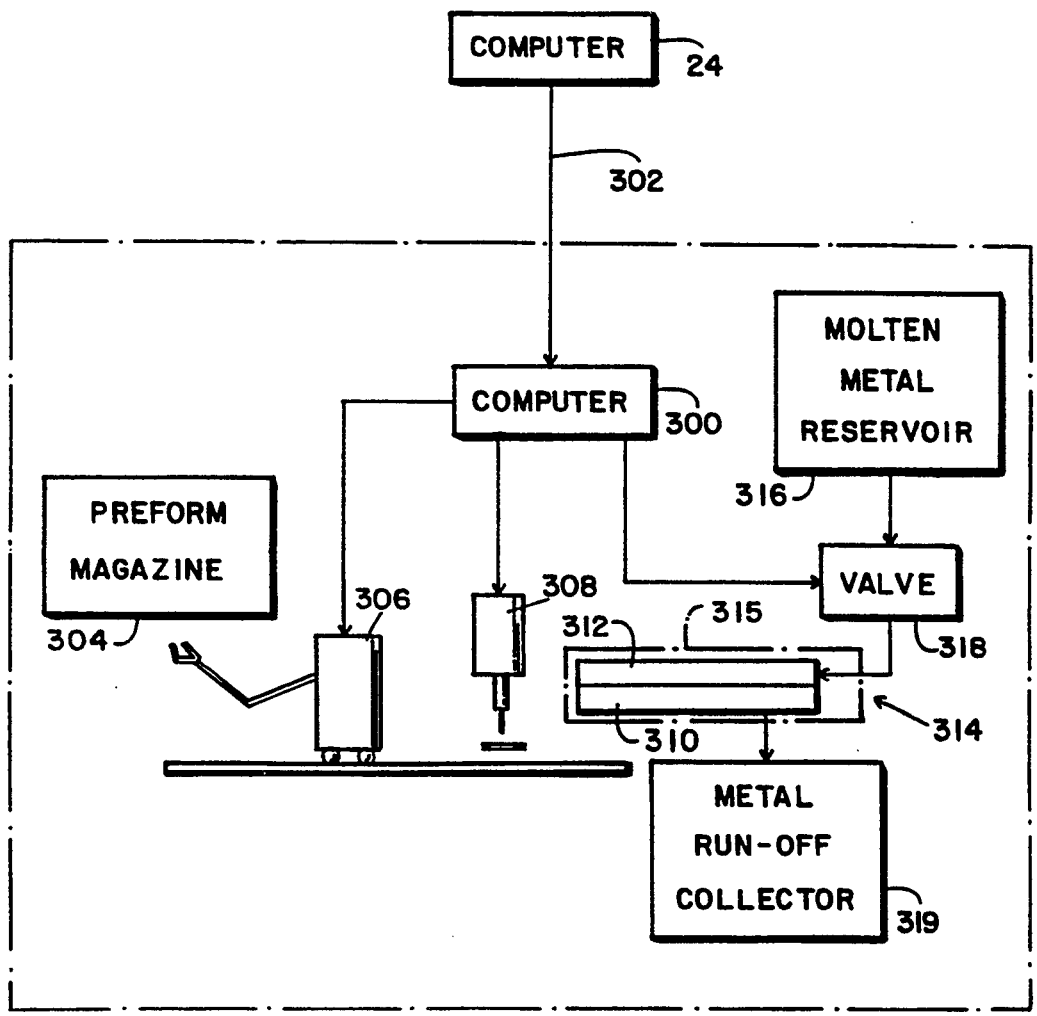
FIG. 18 is a diagram of a system for manufacturing a dental prosthesis, in accordance with the present invention.

As illustrated in FIG. 18, to manufacture a metallic substructure of a dental prosthesis such as a crown, bridge or filling, computer 24 is operatively connected to another computer 300 at a remote location via a telecommunications link 302 such as the telephone lines. In response to an instruction from an operator, computer 24 transmits to computer 300 an electrical signal encoding geometric specifications of the metallic substructure of the prosthesis. The specifications include the dimensions and shape of a tooth preparation at a dental site at which the prosthesis is to be affixed and configuration of the substructure. More particularly, in the event that the dental practitioner wishes to provide a tooth with a crown, the three-dimensional surface of a preparation of the tooth is encoded by computer 24 and transmitted as part of an order signal to the remote computer 300.

As described hereinabove, the three-dimensional surface data of the tooth preparation may be derived from three-dimensional data of the tooth by instructing the computer to modify the tooth surface data to produce, in electronic form and as visually presented on monitor 34 (FIG. 1), a desired tooth preparation. The computer may be instructed, for example, via keyboard 40 (FIG. 1), a mouse (not shown), or a contact sensitive surface of monitor 34, to remove from the electronic representation of the tooth a resective percentage of the dental matter electrical data representing a three-dimensional surface of a desired tooth preparation are discussed in detail hereinabove. Alternatively, the tooth may actually be prepared, the electrical signal transmitted to remote computer 300 from computer 24 in that case corresponding to an actual preparation, rather than a planned preparation. The three-dimensional surface data of the actual tooth preparation may be accumulated by any of the methods deescribed above.

The electrical data transmitted from computer 24 to computer 300 also includes a specification of the type and thickness of the crown or other dental prosthesis for which the dental practitioner is placing an order.

Computer 300 is located at a manufacturing facility which maintains in a store or magazine 304 an inventory of dental mold preforms corresponding to a multiplicity of tooth preparations for each tooth position. The preform magazine also includes a multiplicity of cooperating preforms each serving to define the outer surface (opposite the prepared tooth surface) of a metallic portion of a respective dental prosthesis substructure. Computer 300 maintains a registry of all the available preforms.

Figure 19:
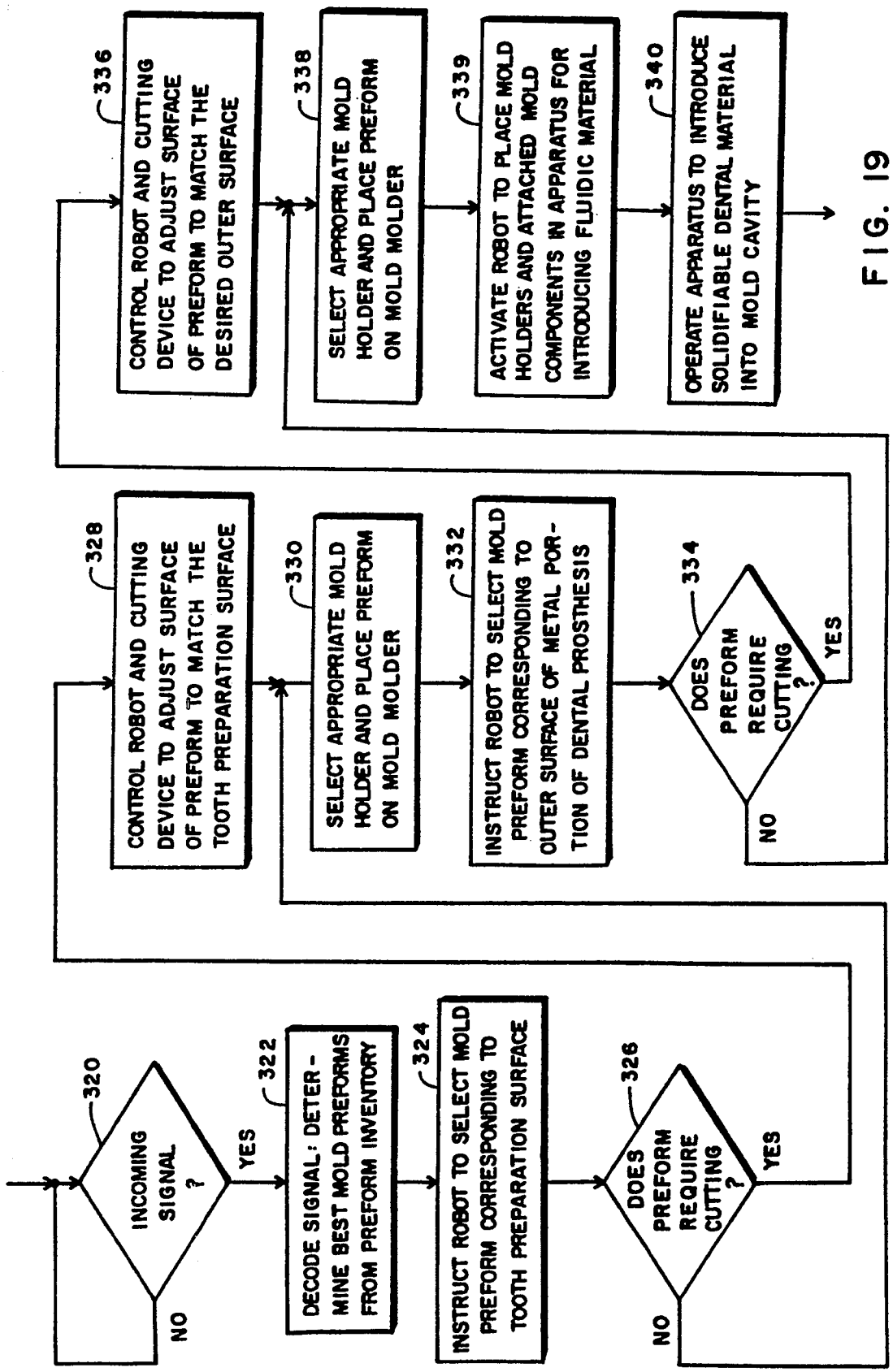
FIG. 19 is a flow chart showing successive steps in the operation of a control unit or computer in the system of FIG. 18.

As indicated in FIG. 19, computer 300 monitors telecommunications link 302 in a recurring step 320 to determine whether an order has arrived for a dental prosthesis. Upon detecting such an order, computer 300 decodes the signal in a step 322 and in response to the information contained in the signal, selects a mold preform from magazine or store 304 which corresponds most closely to the three-dimensional dental preparation encoded in the received signal. Upon making the selection from its memory banks, computer 300 instructs a robot mechanism 306 (FIG. 18) in a step 324 (FIG. 19) to physically obtain the selected mold preform from magazine 304.

In an inquiry 326, computer 300 determines whether the selected mold preform has a three-dimensional molding surface corresponding identically to the three-dimensional tooth preparation or whether the mold preform requires machining to attain the exact surface required. If machining is necessary, computer 300 instructs (in a step 328) robot mechanism 306 to place the preform in a cutting device 308. Computer 300 then operates the cutting device to machine the preform mold until the correct surface characteristics are attained.

In a subsequent step 330, computer 300 generates an output signal controlling robot mechanism 306 to select a mold holder or support 310 for the preform and to place the machined preform thereon.

Computer 300 then scans its memory banks for a cooperating preform in magazine 304 having a surface most closely corresponding to the outer surface (opposite the tooth preparation surface) and configuration of the desired dental prosthesis substructure, as encoded in the signal recieved over telecommunications link 302 from computer 24. Upon selecting the cooperating preform, computer 300 instructs robot mechanism 306 to extract that preform from magazine 304 (step 332, FIG. 19). In an inquiry 334, computer 300 checks whether the selected cooperating preform requires cutting to produce the required mold surface. If cutting is required, computer 300 controls robot mechanism 306 and cutting device 308 to perform the necessary cutting operations on the cooperating preform (step 336). In a subsequent step 338, computer 300 activates robot mechanism 306 to select another mold holder or support 312 and to attach the machined cooperating preform thereto.

Upon the positioning of the machined preforms or mold components in mold holders 310 and 312, robot mechanism 316 acts under the control of computer 300 to place the mold holders 310 and 312 and attached mold components into an apparatus 314 for introducing a quantity of a fluidic solidifiable dental material into the mold cavity defined by the two mold preforms or components. Apparatus 314 exemplarily takes the form of an injection molding machine, a casting machine or an injection press (see FIG. 26). Apparatus 314 includes a reservoir or store 316 of the fluidic solidifiable dental material which may be a metal or metal alloy or other dental composition. In a step 340, computer 300 operates apparatus 314, for example, through a valve 318, to introduce the fluidic dental material, e.g., molten metal, into the mold cavity. A collector 319 is provided for catching excess metal. The excess metal is then returned to reservoir 316.

Figure 20:
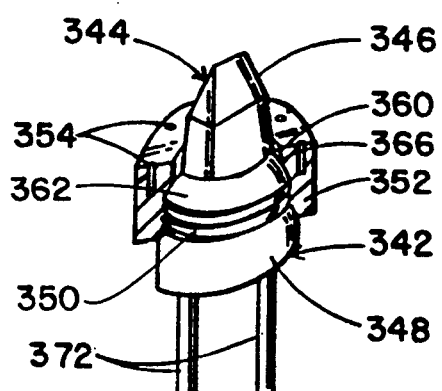
FIG. 20 is a perspective view, partially in cross-section, of a mold component usable in the system of FIG. 18 for forming a metal substructure portion of a crown.
Figure 21:
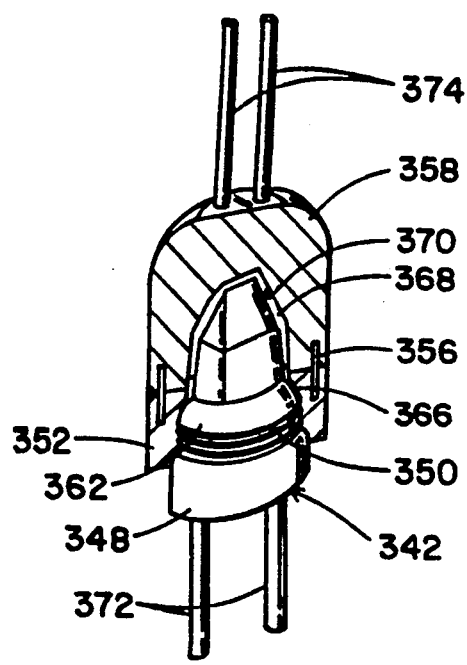
FIG. 21 is a perspective view, partially in crosssection, of the mold component of FIG. 20 in juxtaposition with another mold component, thereby forming a mold cavity for casting, injection molding or press molding a crown.
Figure 22:
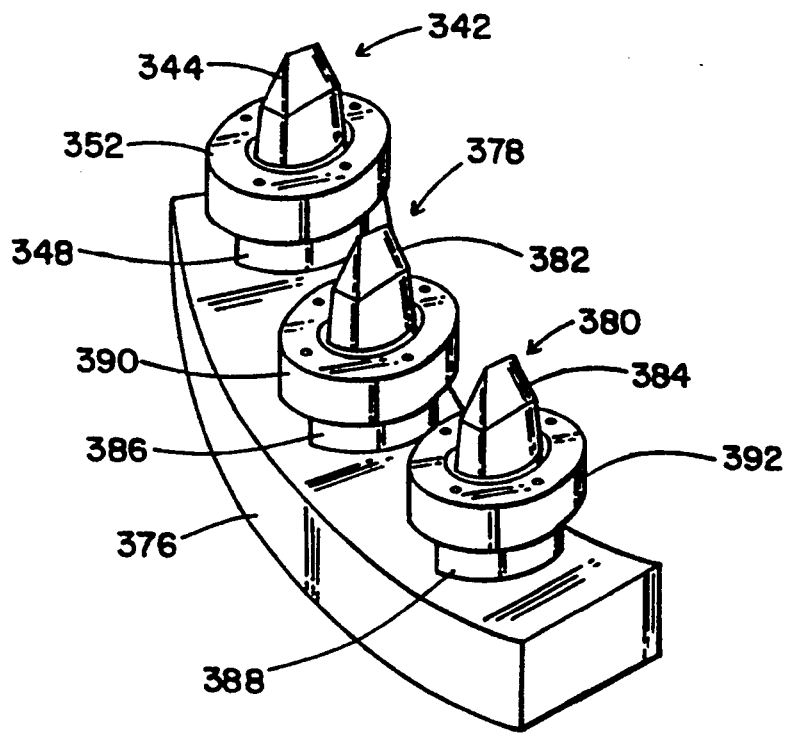
FIG. 22 is a perspective view of a plurality of mold components substantially similar to the mold component of Fig. 20, all attached to a mold holder or support in accordance with the invention.

As depicted in FIGS. 20, 21 and 22, a mold preform or component 342 has a body 344 with a surface 346 corresponding to the surface of a dental preparation (either actual or planned) as specified in the signal arriving at computer 300 over telecommunications link 302 from computer 24. Body 344 of mold preform 342 is provided with a base portion 348 in turn provided with an external screw thread 350 which meshes with an internal screw thread (not separately designated) of an annular mold part or ring 352.

Ring 352 is provided with plurality of circumferentially spaced, axially extending bores 354 for receiving respective connector or guide pins 356 extending from another mold preform or component 358. Ring 352 is also provided with an inner surface 360 which is machinable to provide a close tolerance in cooperating with a corresponding surface 362 of mold component 342 to form a skirt portion 366 of a mold cavity 368. Skirt portion 366 of mold cavity 368 produces a gingival skirt extension (not shown) of a cast dental prosthesis substructure (not shown). Because the gingival skirt extension may extend to fit between the tooth and the gum of the patient, it is necessary that the extension be made very thin and is produced with a strict or narrow tolerance.

Mold component 358 has an inner surface 370 corresponding to an outer surface (opposite the prepared tooth surface) of a metallic portion of a respective dental prosthesis substructure. Surface 370 cooperates with surfaces 346 and 360 to define mold cavity 368.

As described hereinabove with reference to FIGS. 18 and 19, mold components 342 and 358 are machinable, particularly on surfaces 346 and 370, to provide mold cavity 368 with the precise surfaces, dimensions and configuration requested by the dental practitioner in the signal transmitted from computer 24 to computer 300 over link 302 (FIG. 18). Although ring 352 may be incorporated as a unitary or integral part of mold component 342, under certain conditions where marginal requirements are not easily machined, it is advantageous to provide the ring as a separate component to facilitate the machining of surface 360.

It is to be noted that the machining operation, carried out, for example, by cutting device 308 in FIG. 18, may be accomplished by any of a number of well known methods. Such methods include drilling, laser etching, ultrasonic material removal and electroerosion.

It is to be further noted that the machining operations are carried out on the preforms or mold components 342 and 358, rather than on a cast metallic blank. This results in a reduction in machining times and costs since great numbers of mold blanks of various geometries can be kept in stock, enabling a very close fit selection of the desired part number to be used. Little or no machining of the finished metal casting, coping, crown, inlay or other product is required, thereby maintaining the integrity of the piece and minimizing if not eliminating the introduction of stress points and fatigue or gaseous elements locked into the metal substructure product. As discussed hereinafter, the use of the described method to produce multiple tooth prostheses such as bridges will also contribute to the strength and longevity of those dental appliances by eliminating gaseous elements inherent in castings, and by eliminating the necessity for soldering, which naturally introduces stresses into the bridge material.

As shown in FIGS. 20 and 21, mold components 342 and 358 are provided with elongate rods or pins 372 and 374 for releasably attaching the mold components to respective mold supports, e.g., mold holder 376 in FIG. 22. As shown in that drawing figure, mold holder 376 carries a plurality of mold components 342, 378 and 380 each including a respective body portion 344, 382 and 384, base portion 348, 386 and 388, and ring or flange 352, 390 and 392. Mold components 342, 378 and 380 are spaced from one another and correspond to different teeth, possibly of different patients, perhaps even patients of different dental practitioners. Computer 300 (FIG. 18) is programmed to place several mold components such as component 342 or 358 on the same mold holder to thereby provide for the production of several dental prosthesis substructures simultaneously.

Figure 23:
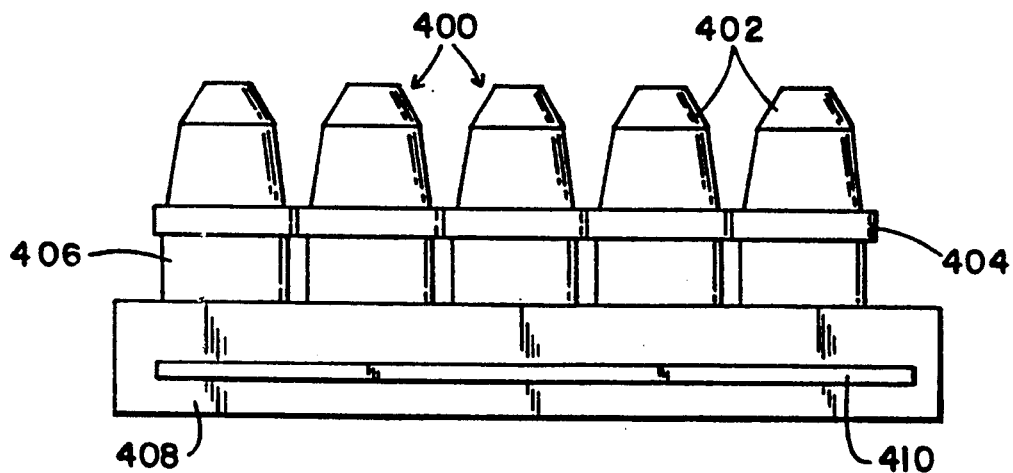
FIG. 23 is a diagrammatic side elevational view of a mold support carrying a plurality of inner mold components corresponding to respective adjacent teeth in the mouth of a single patient.

Alternatively, if required by a particular patient's dental condition, a bridge or splint can be produced using the techniques described herein. As illustrated in FIG. 23, a plurality of mold components 400 having body portions 402, gingival rings or flanges 404 and base portions 406 are connected in an arcuate array (not visible in diagrammatic illustration of FIG. 23) to a mold holder or support member 408. Mold holder 408 is provided with releasable attachment elements such as grooves or ribs 410 for facilitating the attachment of the mold holders to a molding machine (see FIG. 26 and the accompanying description). Body portions 402 of mold components 400 have surfaces which match the surfaces of respective tooth preparations (actual or planned) such as full crown forms shaped as posts to which a patient's teeth have been reduced or are to be reduced.

Figure 24:
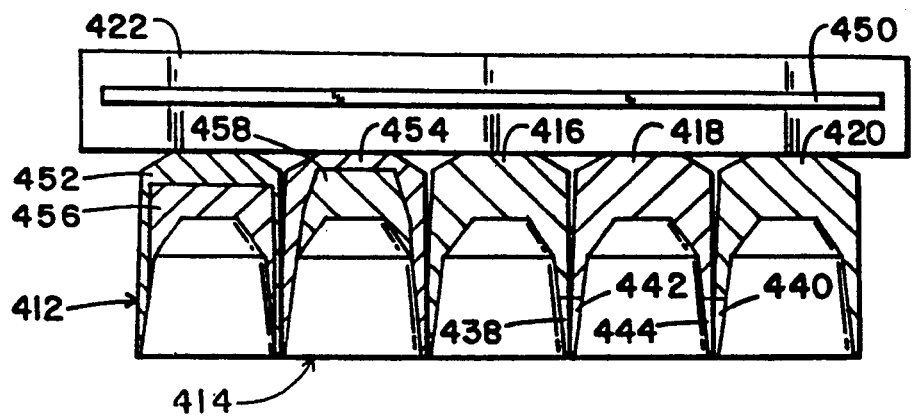
FIG. 24 is diagrammatic side elevational view of a mold support carrying a plurality of outer mold components corresponding to the inner mold components of FIG. 23.
Figure 25:
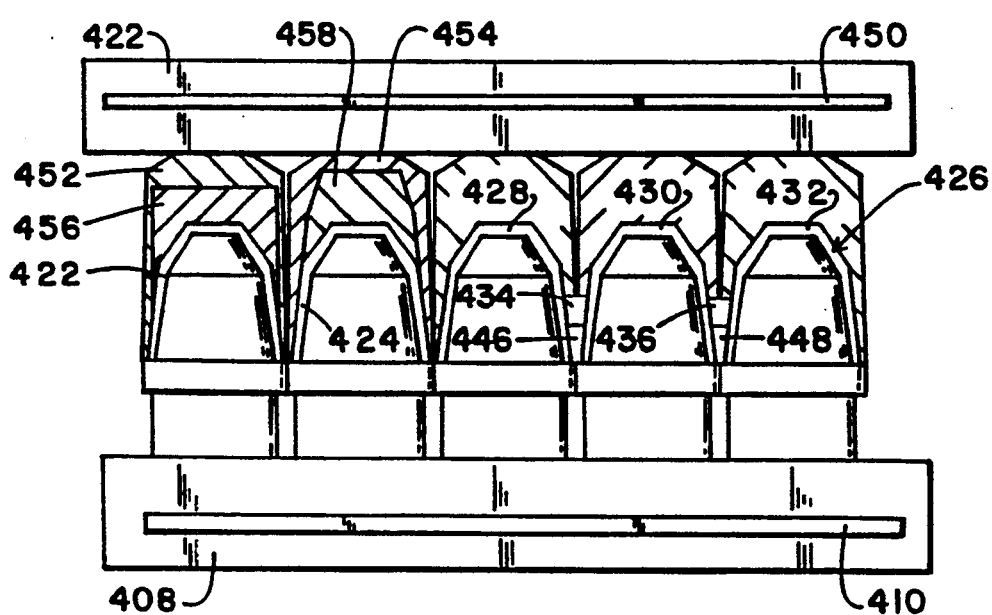
FIG. 25 is a diagrammatic side elevational view of the mold supports and inner and outer mold components of FIGS. 23 and 24, showing the mold components disposed in fitted juxtaposition to one another to form a plurality of mold cavities for forming the metal or allow substructures of a pair of crowns and a bridge.

As depicted in FIG. 24, a plurality of mold components 412, 414, 416, 418 and 420 for forming the outer surfaces (non-tooth-contacting surfaces) of dental prostheses for a single patient's mouth are secured to a mold holder or support 422 in an arcuate array matching the array of FIG. 23. As depicted in FIGS. 23 and 24, mold components 400 are inner or male mold components, while components 412, 414, 416, 418 and 420 are outer or female mold components. The inner mold components 400 are at least partially inserted into respective ones of the outer mold components 412, 414, 416, 418 and 420, as shown in FIG. 25, to form a plurality of mold cavities 422, 424 and 426. Mold cavities 422 and 424 correspond to individual teeth, i.e., form the metal portions of respective crowns, while mold cavity 426 comprises three crown-shaped spaces 428, 430 and 432 connected by bridging spaces 434 and 436 to form a bridge prosthesis, wherein units are attached or splinted to each other.

As illustrated in FIG. 24, mold components 416 and 420 are each provided in a side wall with a respective slot 438 and 440, while mold component 418 is provided in opposite side walls with a pair of slots 442 and 444 essentially coextensive with slots 438 and 440, respectively. After the automatic insertion of inner mold components 400 into outer mold components 412, 414, 416, 418 and 420, a first wedge 446 is automatically inserted into communicating slots 438 and 442 and a second wedge 448 is inserted into communicating slots 440 and 444, thereby defining bridging spaces 434 and 436.

Figure 26:
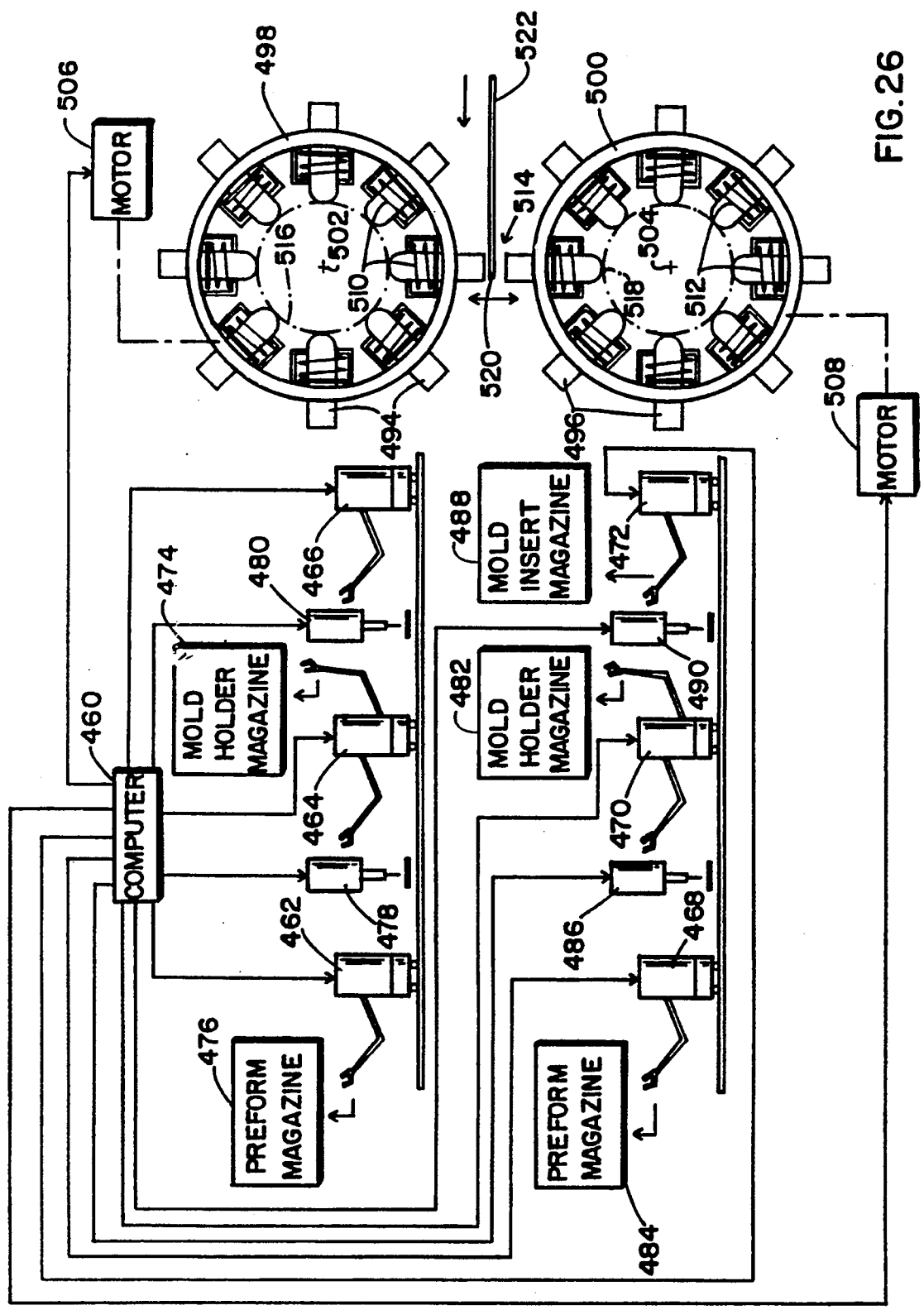
FIG. 26 is a diagram of another system for manufacturing a dental prosthesis, particularly for manufacturing a metal or alloy substructures of the prosthesis

Mold holder or support member 422 is provided with at least one attachment member such as a groove or rib 450 for facilitating the attachment of the mold holders to a molding machine (see FIG. 26 and the accompanying description).

As further illustrated in FIGS. 24 and 25, outer mold components 412 and 414 comprise respective outer mold parts 452 and 454 into which inserts 456 and 458 have been placed for adapting mold parts 452 and 454 to conform to the electrically encoded three-dimensional surface of the respective dental prosthesis substructure, as transmitted from computer 24 to compter 300 over link 302 (FIG. 18). The inserts are obtained from a store or magazine of mold inserts and may be machined as described herein to conform the operative surfaces of the inserts to the three-dimensional data received from dental practitioners.

A mold assembly as shown in FIGS. 23 and 24 may be retained as a separate inventory piece or stock item subsequently to the use thereof. A manufacturing facility operating pursuant to the methods described herein builds its inventory of mold components and mold assemblies (i.e., bridges, splints and other multiple tooth type mold units) by accumulating the used mold components and mold assemblies. Computer 300 controls the arrangement and rearrangement of the stock items and continually updates its memory registry thereof.

As illustrated in FIG. 26, another system for manufacturing dental prosthesis substructures comprises a remote computer 460, analogous to computer 300 in FIG. 18 and connectable via telecommunications link 302 to a multiplicity of local computers such as computer 24 in FIG. 1. Computer 460 is operatively connected to a plurality of robot mechanisms 462, 464, and 466 for forming a first mold assembly, for example, the inner mold component assembly of FIGS. 23 and 25. Computer 460 is also operatively connected to another plurality of robot mechanisms 468, 470, and 472 for forming a second mold assembly, for example, the outer mold component assembly of FIGS. 24 and 25, which cooperates with the first mold assembly to form a plurality of dental mold cavities or chambers.

Upon receiving a signal identifying a substructure for a complex three-dimensional dental prosthesis such as a bridge, computer 460 scans its internal memory banks for a mold component assembly having at least two mold components closely corresponding in three-dimensional surface configuration to respective tooth preparation surfaces of the requested bridge. Upon selecting such a mold assembly, computer 460 activates robot mechanism 464 to retrieve the selected mold assembly from an inventory magazine 474 of mold holders including previously made mold assemblies such as that shown in FIG. 23.

As described hereinabove with reference to FIGS. 18 and 19, computer 460 then selects from its memory banks one or more mold components for teeth not having a corresponding mold component on the selected mold assembly. Computer 460 operates robot mechanism 462 to retrieve the selected mold components from a preform magazine 476 and to place the selected components in a cutting or machining device 478. Machining device 478 is operated under the control of computer 460 to conform the operative surfaces of the selected mold components to the respective electrically encoded three-dimensional surface data of the tooth preparations. In response to signals received from computer 460, robot mechanism 464 removes the finished mold component or components from machining device 478 and places them in proper positions on the selected mold assmbly unit.

Alternatively, if a suitable previously manufactured mold assembly is not available in the inventory of the manufacturing facility, computer 460 operates robot mechanisms 462 and 464 to prepare a new assembly from the basic stock mold components. In that event, a blank mold holder (not illustrated) is obtained by robot mechanism 464 from magazine 474. Under the control of signals from computer 460, robot mechanism 464 and another machining device 480 drills holes in the mold holder in relative locations corresponding to the array of tooth preparations for the bridge. The mold holder is provided with two bores for each mold component or preform obtained by robot mechanism 462 from preform magazine 476, the bores determining the position and orientation of the respective mold component in the array. The position and orientation of the mold component in the array is based on analysis and computation of the original surface data digitized into the system.

While robot mechanisms 462 and 464 are working on a mold assembly of inner mold components (see FIGS.

23 and 25), computer 460 controls robot mechanisms 468 and 470 to assemble a mold component assembly of outer mold components (see FIGS. 24 and 25). If a suitable previously manufactured mold assembly exists in a mold assembly and mold holder magazine 482, robot mechanism 470 retrieves the mold assembly pursuant to signals from computer 460. Also under the control of computer 460, robot mechanism 468 retrieves additional or replacement mold components from a preform magazine 484 and positions them in a machining apparatus 486 which cuts the preforms or mold components to the specifications obtained from the dental practitioner as described above. In the event that one or more outer mold components (see reference designations 412 and 414 in FIGS. 24 and 25) require inserts to adapt them to the specification from the practitioner, computer 460 commands robot mechanism 472 to retrieve appropriate mold inserts (e.g., inserts 456 and 458 in FIGS. 24 and 25) from a store or magazine 488 of mold inserts. In response to signals from the computer, robot mechanism 472 and an additional machining apparatus 490 cooperate to machine the inserts to the prosthesis specifications from the dental practitioner.

Upon the assembly of the outer mold components and the inserts by robot mechanisms 470 and 472, computer 460 controls one or the other robot mechanism to obtain wedges (e.g., 446 and 448 in FIG. 25) for insertion between adjacent mold components in the bridge mold assembly. The wedges are obtained from an inventory in a magazine (not shown) and may be machined for exact fit within close tolerance ranges.

Upon the completion of the inner and outer mold component assemblies, robot mechanisms 466 and 472 attached the mold assemblies to respective piston or plunger members 494 and 496 which are reciprocatingly mounted to respective drums 498 and 500. Drums 498 and 500 are step-wise rotated about respective axes 502 and 504 by motors 506 and 508 energized under the control of computer 460.

Each plunger member 494 and 496 is biased towards a radially inward position by a respective tension spring 510 and 512 (compression springs may be used instead). When the plunger members 494 and 496 reach a nip 514 between the two drums 498 and 500, the plungers members are pushed towards one another, for example, by camming surfaces 516 or 518 or any other technique (such as pneumatic cylinders, not shown).

During the insertion of the inner mold components into the respective outer mold components occasioned by the pushing of plunger members 494 and 496 towards one another, a free end 520 of a continually advancing ribbon 522 of fluidic solidifiable dental material such as a precious metal or alloy in a hot semi-solid form is sheared off and assumes the form of the mold cavity or cavities defined by the inner and outer mold components diposed in the juxtaposed plunger members 494 and 496. Upon a subsequent rotation of drums 498 and 500 by motor drives 506 and 508 under the control of computer 460, the mold components are separated from one another and the molded dental prosthesis substructure thereby made available for removal and shipment to the dental practitioner who ordered the prosthesis substructure. A layer of porcelain or other cosmetic covering may be applied to the outer surface of the dental prosthesis substructure prior to shipment.

In an alternative manufacturing scenario, a portion of the above-described manufacturing steps are performed at one location by one party, while other steps are performed at another location by another party. Specifically, a supplier of dental compositions such as precious metals and alloys is equipped with an inventory of mold components, mold inserts and mold supports for producing nearest net shapes or blanks. In response to an order from a dental laboratory for a substructure of particular type of dental prosthesis (crown, bridge, etc.) having specified dimensions and surfaces as described hereinabove, the supplier sends to the laboratory a blank of precious metal or alloy having dimensions slightly larger than the dimensions of the ordered prosthesis substructure. In addition, the supplier might send mold components for producing from the blank the ordered prosthesis substructure in accordance with the methods described hereinabove with reference to FIGS. 18, 19 and/or 26. In that event, the supplier also transmits to the dental laboratory, for example, on a floppy disk or other electronic stroage medium accompanying the blank and the mold components, an electrical signal encoding the three-dimensional surface characteristics of the mold components.

The dental laboratory, upon receiving the slightly oversized nearest net shape or blank from the supplier, prepares the mold components for press molding the desired prosthesis substructure from the blank. This preparation entails minor machining of the mold components, if necessary, as described hereinabove. The prepared mold components, together with the oversized nearest net shape or blank, are placed in an oven and heated to a predetermined press molding temperature appropriate to reduce the material of the precious metal or alloy or other solidifiable dental composition to a fluidic semisolid state capable of fluid flow under pressure. Then the mold components are pressed together, with the dental substructure blank inserted therebetween, to apply a compressive pressure to the blank to eliminate inaccuracies in the blank's shape. Any excess metal or alloy, which will be limited to a small amount, is squeezed from between the mold components during the press molding process and may be sliced off and collected for return to the supplier.

Upon a subsequent cooling of the molded prosthesis substructure, a porcelain layer is applied to an outer surface of the substructure by techniques similar to those described above with respect to the manufacture of the substructure. The laboratory prepares the porcelain layer in accordance with an specifications encoded in the electrical signal which it has received from a dental practitioner as part of an order for the completed dental prosthesis. In particular, the dental laboratory removes the outer or female mold component(s) from the press molded prosthesis substructure(s), while retaining that substructure(s) on the inner or male mold component(s). A cavity or space formed by another outer or female mold component is then filled with a fluidic porcelain composition. This other outer or female mold component has an inwardly facing surface which conforms to the outer surface of the porcelain layer of the dental prosthesis, as specified in the order placed by the dental practitioner. Upon an introduction of the fluidic porcelain material into the outer mold component, the original inner mold component holding the press molded prosthesis substructure and the new outer mold component holding the fluidic porcelain material are moved into mating juxtaposition with one another so as to press the fluidic porcelain material to the outer surface of the press molded prosthesis substructure. This process is carried out at temperatures suitable to the maintenance of a suitable viscosity to the fluidic porcelain material.

Figure 27:
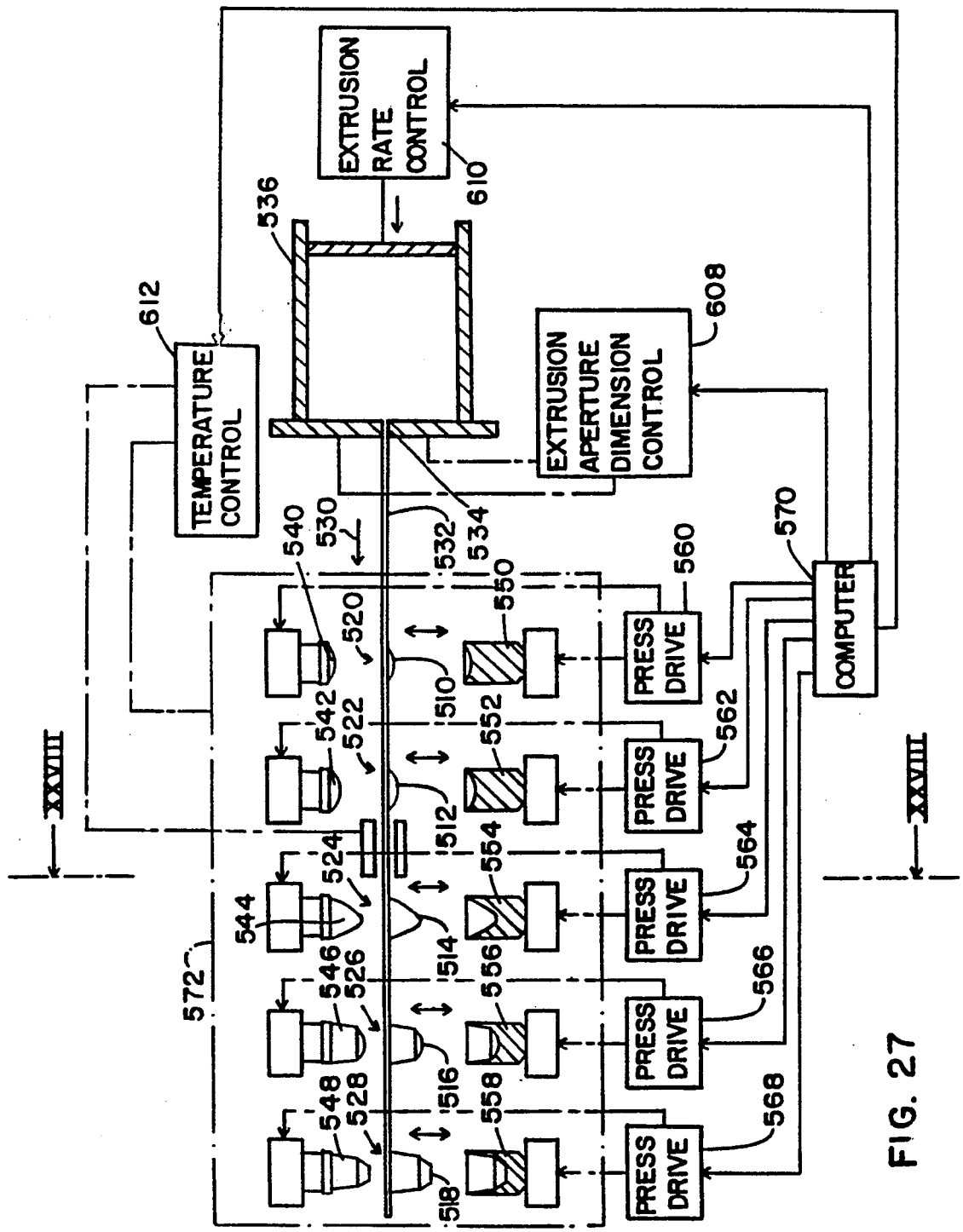
FIG. 27 is a diagrammatic representation of yet another system for manufacturing a dental prosthesis, particularly for manufacturing a metal or alloy substructure of the prosthesis.
Figure 28:
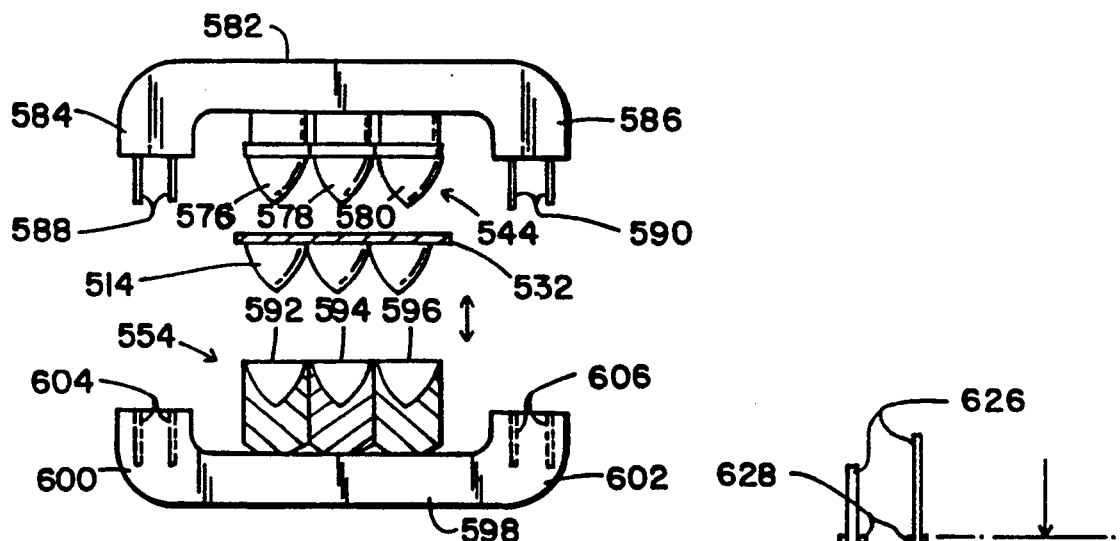
FIG. 28 is a view taken along line XXVIII—XXVIII in FIG. 27.

As shown in FIGS. 27 and 28, a metal substructure of a dental prosthesis such as a three-unit bridge or splint is advantageously fabricated through an incremental press molding process in which successive approximations 510, 512, 514, 516, 518 of the final product are pressed at a series of press molding stations 520, 522, 524, 526, and 528 spaced along a feed path or direction 530 of a continuously cast or extruded ribbon or strip 532 of precious metal, alloy or other maleable and deformable dental material. Ribbon 532 emerges from an aperture 534 of a continuous casting or extrusion machine 536 where the deformable dental material is maintained in a fluidic state by elevated temperatures and pressures.

At each molding station 520, 522, 524, 526, and 528, a respective male or inner mold component 540, 542, 544, 546 and 548 is pressed towards and partially into a respective female or outer mold component 550, 552, 554, 556 and 558 by a respective drive mechanism 560, 562, 564, 566 and 568 controlled by a computer 570 analogous to computer 300 in FIG. 18 and connectable via telecommunications link 302 to a multiplicity of local computers such as computer 24 in FIG. 1. Drive 560 is operated first to form dental substructure approximation 510 from ribbon or strip 532. Ribbon 532 then advances to station 522 where drive mechanism 562 presses male or inner mold component 542 into female or outer mold component 552 to form approximation 512. approximations 514, 516, and 518 are formed at successively later times at respective stations 524, 526, and 528.

As indicated schematically by a dot-dash line, the successive approximation press molding procedure may take place in an oven chamber 572 at suitably elevated temperatures. Additionally or alternatively, ribbon or strip 532 may be maintained at elevated temperatures by a plurality of heater devices 574 (only one shown in the drawing) disposed along the path of ribbon 532 between stations 520, 522, 524, 526, and 528.

A successive approximation process in accordance with the invention facilitates the production of the finished dental prosthesis substructures and results in a superior product owing the the continual annealing of the dental material during the process and particularly between successive press molding operations.

As illustrated particularly in FIG. 28, male or inner mold component 544 (like the other male or inner mold components 540, 542, 546 and 548) includes a plurality of male mold elements 576, 578 and 580 mounted in an appropriately arced array to a mold support or holder member 582 formed at opposite ends with a pair of arms 584 and 586 in turn provided at their ends with guide pins 588 and 590. Similarly, female or outer mold component 554 (like the other female or outer mold components 550, 552, 556 and 558) includes a plurality of female mold elements 592, 594 and 596 mounted in a similarly arced array to a mold support or holder member 598 provided at opposite ends with a pair of arms 600 and 602 in turn provided at their ends with bores 604 and 606 for receiving guide pins 588 and 590 during a mold closing motion.

Upon receiving from computer 24 (FIG. 1) electrical signals encoding the three-dimensional surface characteristics of a bridge, computer 570 selects male or inner mold components 540, 542, 544, 546 and 548 and female or outer mold components 550, 552, 554, 556 and 558 from an inventory of such mold component, as described hereinabove. Such mold components may be machined, if necessary. In addition, one or more of the female or outer mold components 550, 552, 554, 556 and 558 may comprise an outer mold body and an insert or nest element, as described in detail above with reference to FIGS. 24 and 25.

Upon selecting the male or inner mold components 540, 542, 544, 546 and 548 and the female or outer mold components 550, 552, 554, 556 and 558, computer controls the disposition thereof by robot mechanisms (not shown in FIGS. 27 and 28) at press mold stations 520, 522, 524, 526, and 528, as described hereinabove with reference to FIG. 26. Press mold stations 520, 522, 524, 526, and 528 may particularly take the form of respective pairs of drums with slidably mounted pressure members, as described in detail above with reference to FIG. 6. Other possible press mold realizations within the contemplation of the invention include conventional hydraulic and pneumatic mechanisms controllable by computer 570.

Computer 570 is capable of overseeing the manufacture of several dental prosthesis substructures simultaneously. Thus, ribbon 532 may be formed along its length with a continuous sequence of approximating forms for different dental prostheses. Because each prosthesis comprises a unique combination of dental forms and a substructure having a specific unique volume, the amount of material required, as well as molding temperatures and the number of requisite approximations will vary from prosthesis to prosthesis. Based on the digitized surface information included in the electrical signals arriving from practitioners, either directly or through dental laboratories, computer 570 is accordingly programmed to calculate and implement variations in such processing parameters as the thickness of ribbon 532 and the temperature thereof, as well an the number and degree of the successive approximations for each individual prosthesis. Computer 570 generates signals transmitted to a device 608 for instantaneously controlling the height and/or width of extrusion aperture 534 to accord with the material requisites of the series of prosthetic substructures. The rate at which ribbon 532 advances is also controlled by computer 570 through an extrusion rate control device 610. Temperatures of ribbon 532 along its length are controlled by computer 570 via a temperature control device 612.

As described above, a prefinal approximation (e.g., approximation 518), together with mold components both for the load bearing substructure and for any surface layer (e.g., porcelain), may be conveyed to a dental laboratory for final operations to produce the complete, finished product.

Figure 29:
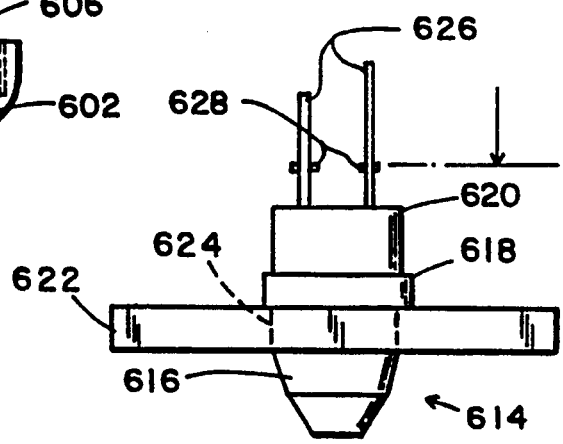
FIG. 29 is a schematic side elevational view of a preformed mold component in a magazine or storage rack.

As shown in FIG. 29, a male or inner mold component 614 including a body portion 616 with a surface conforming to a dental preparation, a gingival ring structure 618 and a base or stem portion 620 is stored on a magazine rack 622 accessible by a robot mechanism in accordance with the invention. Body portion 616 extends through an aperture 624 in rack 622, while ring structure 618 rests thereon. Base or stem 620 carries a pair of locating pins or fingers 626, each provided with at least one projection 628 in the form of a nub or rib. All male and female mold components described herein are provided such locating pins or fingers and indexing projections to facilitate automatic handing of the mold components by the robot mechanisms. During an automatic selection procedure in accordance with the invention, a robot mechanism (not shown in FIG. 29) grasps mold component 614 by sliding a gripping mechanism downwardly over pins 626 until projections 628 are encountered. The robot then locks the mold component into place and proceeds with manipulating the mold component in the steps described above.

Figure 30:
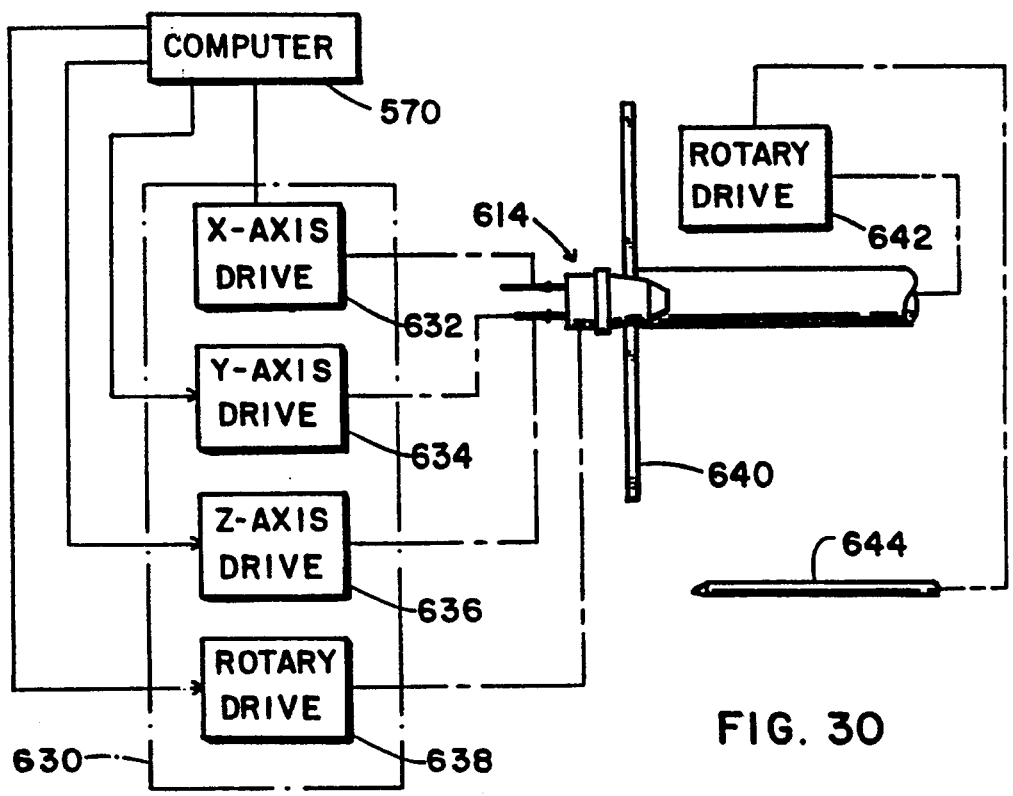
FIG. 30 is a diagrammatic representation of a portion of a system for manufacturing a dental prosthesis.

As depicted in FIG. 30, upon the grasping of mold component 614 by a robot mechanism 630, a computer such as computer 570 in FIG. 27 transmits signals to x-axis drive 632, y-axis drive 634, z-axis drive 636 and/or a rotary drive 638 to control the formation of desired surface characteristics on body portion 616 and in ring structure 618. Through robot mechanism 630, computer 570 controls the extent and nature of material-removing machining on body portion 616 by an abrasive disk 640 rotated at high speed by a drive 642 about an axis extending generally parallel to the axis of mold component workpiece 614. Further features, including the size of a groove formed in gingival ring 618 and surface indentations not formable via disk 640, are machined via a point-milling drill, ultrasonic wave generator or laser tool 644. Numerical control of the mold component workpiece 614 relative to machine tools 640 and 644 is maintained at all times by computer 570.

Upon the completion of machining as illustrated in FIG. 30, a second robot mechanism (not shown in FIG. 30) grasps the mold component 614 by its body portion 616 and places the mold component in a mold holder or support (e.g., 582, 598, FIG. 30) in which the holes for receiving locating pins 626 have already been formed.

It is to be noted that holes or bores formed in a mold component holder or support (see, e.g., reference designations 582 and 598) for receiving locating pins (e.g., 626) have an orientation and depth determined in accordance with the incoming three-dimensional surface information. Even in the event that the prosthetic device is only a crown, the information provided by the dental practitioner includes the relative positions of adjacent teeth and of the opposite tooth forming the bite. The control computer 300, 460 or 570 takes that information into account in determining the angle that a mold component is placed into the respective mold holder prior to a casting or press molding operation as described herein.

An enormous advantage of a system and method in accordance with the invention for producing a dental prosthesis is that milling or machining is minimized and is almost entirely confined to the mold components. The actual substructure and finished product requires little or no machining. Accordingly, accuracies are enhanced over conventional CAD/CAM processes which produce a dental prosthesis by milling from a block-shaped blank.

The methods and apparatus described hereinabove with reference to FIG. 18 can be used to manufacture dental prostheses and restoration appliances such as fillings, crowns, and bridges at a dental practitioner's office. Generally, it is contemplated that such dental appliances are to be fabricated from composite materials and alloys which have relatively low melting points. Such low melting points enable the liquifaction of the dental materials in a relatively small furnace 315 included in apparatus 314 (FIG. 18).

Pursuant to this embodiment of the present invention, the dental practitioner uses optical data generating device 22 (FIGS. 1–10) and mechanical-contact data generating device 26 (FIGS. 1 and 11–17) to provide computer 24 (FIGS. 1, 2 and 8) with three-dimensional surface data of a patient's dentition, including desired external restoration surfaces (which may be substantially identical to the tooth surfaces of the patient's natural dentition) and projected or actual tooth preparation surfaces. Mold forms corresponding to the desired external restoration surfaces projected or actual tooth preparation surfaces are then selected, either by the dentist or automatically by computer 24 via a robot mechanism as described hereinabove with reference to FIGS. 18, 9 and 26. The mold forms or components are preferably made of refractory materials, which are easier to machine than the finished dental materials. The mold forms or components are preferably selected from a kit of such mold forms or components (see FIG. 32). The kit advantageously includes composite dental materials of different colors to facilitate color matching with respect to the patient's natural dentition.

The mold components in the dentist's kit include components such as those shown in FIGS. 20–22. Such mold components can be used to fabricate crowns from low-melting-point substances. The above discussion with respect to FIGS. 20–22 is applicable to a fabrication process implemented in the dental practitioner's offices, except that surface 370 of female mold component or overdie 358 and surface 360 of ring 352 correspond to a desired tooth restoration surface rather than to the surface of a restoration substructure made of metal, alloy or other high-melting-point material.

The procedures described hereinabove with reference to FIG. 18 through 22 are more advantageously used by the dental practitioner to fashion prosthetic dental inserts such as fillings. In that case, the inner surface (see reference designation 370 in FIG. 21) of a female mold component (see reference numeral 358) corresponds to a tooth preparation surface inside a patient's tooth, while the outer surface (see surface 346 in FIG. 21) of the male mold component corresponds to the desired external restored tooth surface.

As illustrated in FIG. 3, computer 24 of a dental data-gathering and control system as described above with reference to FIGS. 1–17 is connected to an electrical power source 750 or other energy control unit for controlling the temperature of a furnace 752 of sufficiently small size and power requirements that it can be located on a dental practitioner's premises. The electrical power output of source 750 is controlled by computer 24 partially in response to input signals from a temperature sensor circuit 751 connected at an input to a temperature sensor 753 located inside furnace 752. Furnace 752 may be essentially of any conventonal furnace type, with modifications as will be apparent from the description hereinafter.

Figure 31:
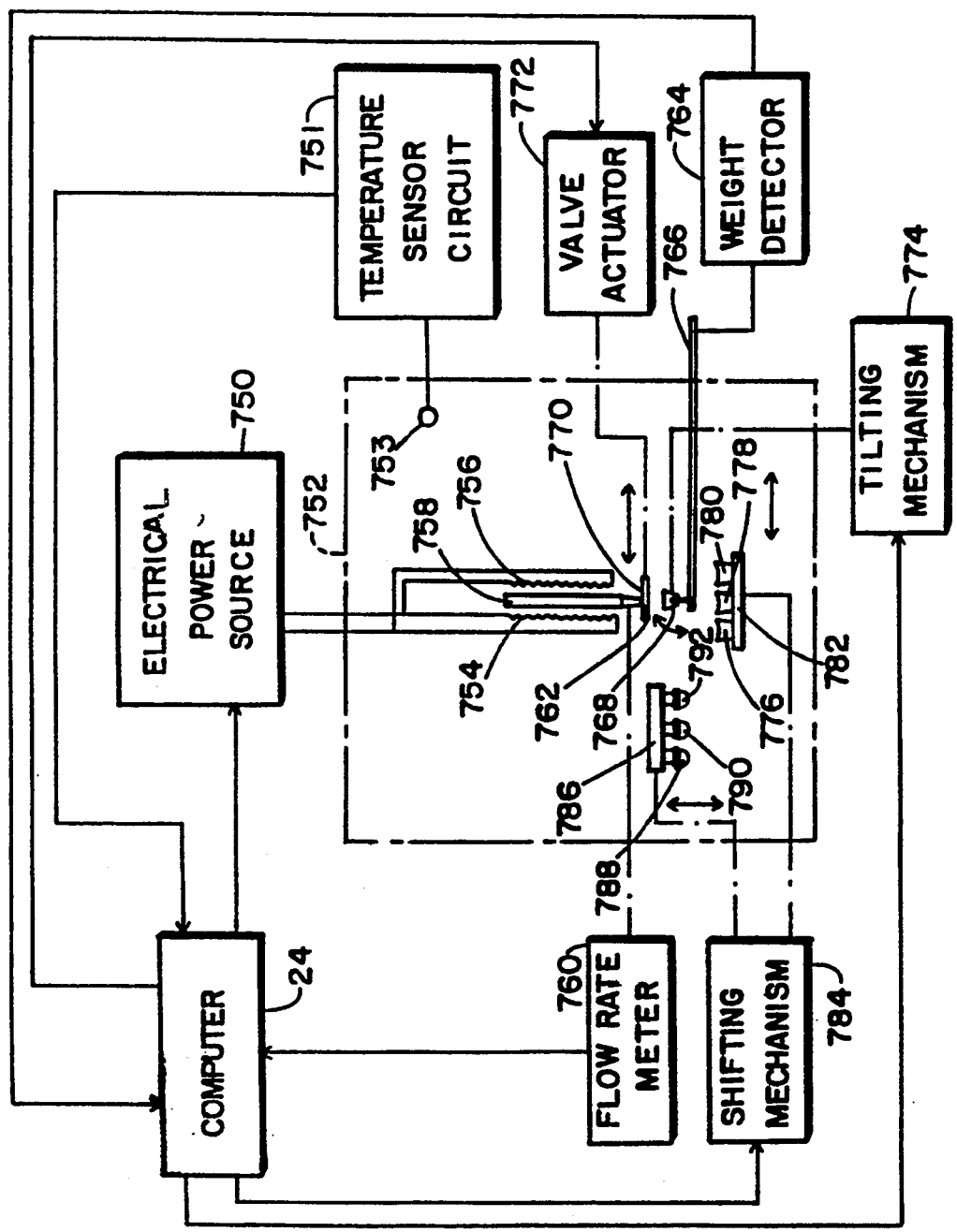
FIG. 31 is a diagram of a furnace system for use in preparing a prosthetic dental appliance in accoradance with the present invention.

Electrical power source 750 is operatively linked to heating elements schematically represented at 754 and 756. Heating elements are juxtaposed to a container 758 which is filled with a charge of fluidic dental material, more particularly liquid or liquifiable dental material such as an at least partially polymeric coventional composite substance. Container 758 may in turn communicate at an inlet (for example, at the upper end as illustrated in FIG. 31) with a reservoir of the dental material (not illustrated).

Computer 24 receives quantity data from a flow rate meter or sensor 760 operatively connected to container 758 for measuring the rate of flow of dental material from an outlet 762 thereof. Computer 24 also or alternatively receives quantity data from a weight detector 764 operatively linked, for example, to a scale type lever arm 766 supporting a small receptacle 768 inside furnace 752. Receptacle 768 is located below outlet 762 for receiving a small amount of flowable dental material upon an opening stroke of a valve member 770 moved by an actuator device 772 under the control of computer 24.

Receptacle 768 is pivotably connected to an end of lever arm 766 and is swung from an upright loading orientation to an angled discharge orientation by a tilting mechanism 774 actuated by computer 24. An aliquot of liquid dental material is poured or dropped from receptacle 768 into a female mold component 776 disposed with other female mold components 778 and 780 on a mold support 782 below receptacle 768.

Mold support 782 together with female mold components 776, 778 and 780, is laterally translatable in two mutually orthogonal horizontal directions by a shifting mechanism 784 functioning under the control of computer 24. In addition, another mold support 786 carrying a plurality of male mold components 788, 790 and 792 in an inverted orientation is vertically translatable by shifting mechanism 784 in response to control signals transmitted thereto by computer 24.

From three-dimensional surface data of a patient's dentition, including desired external restoration surfaces and projected or actual tooth preparation surfaces, and from instructions entered into computer 24 via keyboard 40, computer 24 determines which mold components from a kit of mold components (see FIG. 32) are to be used in fashioning a desired prosthesis or restoration element.

As described hereinabove with reference to FIG. 18, computer 24 can operate mechanical actuator mechanisms or robots to automatically select the best-fit mold components from the inventory in the kit. Upon selection of the mold components, computer 24 controls a cutter such as an electro-erosion or ultrasonic device or a milling machine to modify the operative surfaces (i.e., the surfaces which form the mold cavities) of the mold components to conform those surfaces exactly to the desired tooth restoration surfaces and tooth preparation surfaces identified in electronic form in the memory banks of computer 24. Sometimes machining will not be necessary, when the operative surfaces of the mold components already conform to the tooth restoration surfaces and tooth preparation surfaces.

Upon termination of the machining operations, the selected mold components are automatically placed by the robot mechanism in mold supports 782 and 786 (FIG. 31) and introduced into furnace 752 by shifting mechanism 784. Furnace 752 is heated to a predetermined temperature sufficiently high to melt, or maintain in a liquid state, the dental material selected by the dental practitioner. A charge of that material is placed into container 758 either directly by the dentist or lab technician or indirectly via an automated deposition device (not illustrated). The charge may be in the liquid state prior to deposition into container 758.

Computer 24 automatically calculates the requisite amount of the dental material necessary for forming the filling, crown or other prosthetic appliance. The programming takes into account contraction experienced by the material during a cooling process and may implement calculations based on weight.

Computer 24 energizes actuator 772 to open valve member 770, thereby initiating a controlled flow of the liquid dental material from eye-dropper container 758 into receptacle 768. The amount of material dropping into receptacle 768 is monitored by computer 24 via signals from flow-rate meter 760 and weight detector 764. Upon the deposition of the precalculated amount of dental material into receptacle 768, computer signals actuator 772 to close valve member 770. Tilting mechanism 774 is then operated by computer 24 to tilt receptacle 768 so that the contents thereof are spilled into female mold component 776.

In the event that a plurality of dental prostheses are being formed in furnace 752, computer 24 causes mechanism 784 to shift mold support a predetermined distance corresponding to the distance between mold components 776 and 778. The operations described hereinabove for depositing an amount of dental material into mold component 776 are then repeated for mold component 778. Upon the filling of all mold components on mold support 782, computer 24 induces mechanism 784 to translate mold support 782 into position below mold support 786 and to lower the latter so that male mold components 788, 790 and 792 are inserted into respective female mold components 776, 778 and 780. It is to be understood that the distance that male mold components 788, 790 and 792 are inserted into female mold components 776, 778 and 780 will be zero in the event that the restoration surface is flat, for example, to make a particular kind of filling or filling part.

Figure 32:
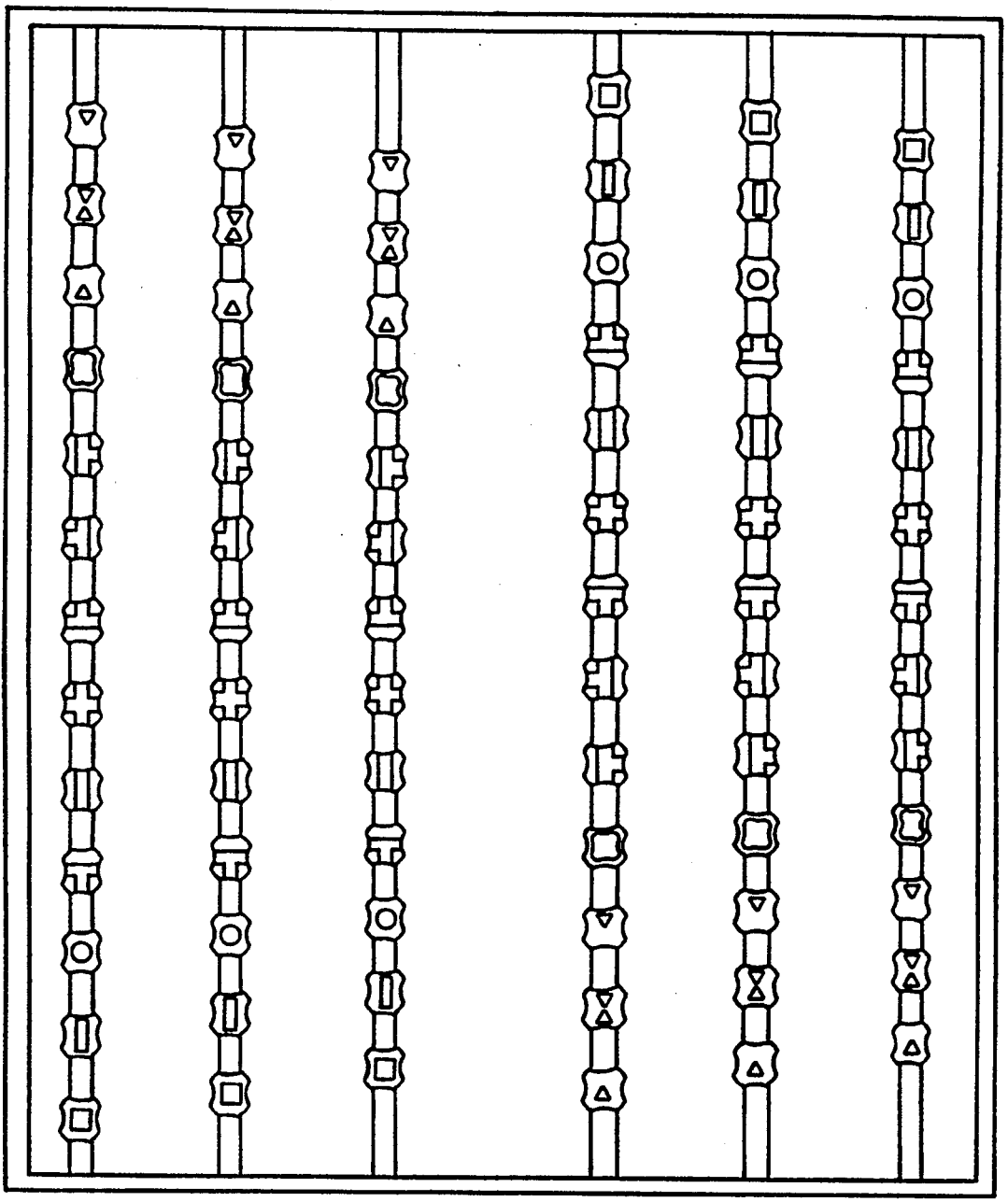
FIG. 32 is a schematic top plan view of a portion of a dental kit in accordance with the present invention.

FIG. 32 schematically illustrates a portion of a dental kit with which dentists and/or labs are supplied in accordance with the invention. The illustrated kit portion includes only female-type filling mold components 794 for teeth of different sizes and for different kinds of fillings. The kit includes a kit box 796 provided with a plurality of elongate grooves 798 for holding mold components 794. Alternatively, the kit box or container may be provided with an array of openings for supporting lod components in the manner illustrated in FIG. 29.

As discussed hereinabove, mold components 794 are preferably made of a relatively soft refractory material which is easily machined. Preferably, the dental kit shown in part in FIG. 32 also includes male mold components for mating with the female mold components to form mold cavities for the formation of fillings and possibly also other dental appliances such as crowns and bridges. Inserts, such as described hereinabove with reference to FIGS. 23-25, may also be included in the kit. In addition, the kit includes dental compositions of different colors for facilitating the matching of patients' dentition.

Figure 33:
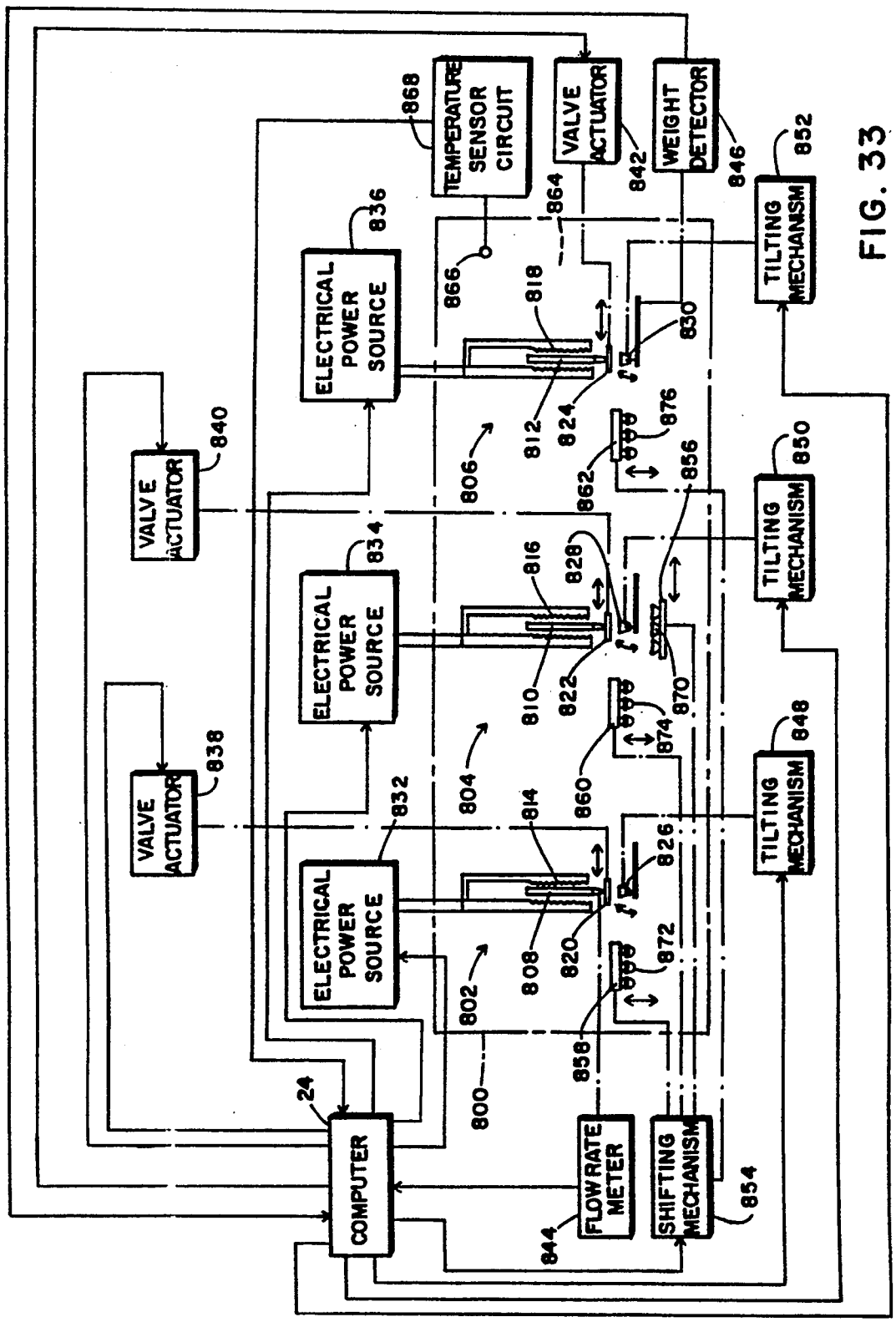
FIG. 33 is a diagram of another furnace system for use in preparing a prosthetic dental appliance in accoradance with the present invention.

FIG. 33 depicts an enhanced furnace assembly for manufacturing, in a dental office or laboratory, more complicated dental appliances each incorporating a plurality of layers of different materials. The furnace assembly includes a furnace 800 provided with a plurality of stations 802, 804 and 806 for forming different layers or parts of dental prostheses. Each station 802, 804 and 806 includes a respective eye-dropper deposition device 808, 810 and 812 with heating elements 814, 816 and 818, a valve 820, 822, 824, and a tiltable receptacle 826, 828, 830. Each deposition station is also provided with a respective electrical power source 832, 834 and 836 for controlling local heating of eye droppers 808, 810 and 812, and a respective valve actuator 838, 840 and 842, as well as respective flow rate meters 844 (only one shown, to simplify the drawing) and respective weight sensors 846 (only one illustrated). Tilting mechanisms 848, 850 and 852 are operatively connected to receptacles 826, 828 and 830 for pivoting those elements, while a shifting mechanism 854 is operatively connected to a lower mold support 856 for translating that support to loading positions under receptacles 826, 828 and 830. Shifting mechanism 854 is also operatively coupled to upper mold supports 858, 860 and 862 for lowering those supports at different stages of a multiple-layer or multiple-part forming process to cooperate with lower mold support 856 to form molded layers or parts of a dental prosthesis.

Upon the commencement of a molding operation, computer 24 monitors the temperature of a furnace chamber 864 via a sensor 866 and associated circuit 868. Further sensors (not shown) may be included for providing computer 24 with feedback regarding local temperature variations within chamber 864, for example, with respect to the temperatures of eye-droppers 808, 810 and 812 and their contents. Computer 24 is programmed to control those temperatures via power sources 832, 834 and 836, as well as to control the timing of various stages in the operation of the furnace assembly.

Computer 24 moves lower mold support 856 from station 802 to station 804 and then to station 806 to deposit controlled amounts of different dental materials into at least one female mold component 870 on mold support 856. After each deposition, shifting mechanism 854 translates lower mold support 856 and the respective upper mold supports 858, 860 and 862 to place male mold components 872, 874, 876 on the upper supports in successive juxtaposition with the female mold component 870. The durations of mold closure are controlled by computer 24 in dependence on temperature and the specific materials being used.

It is to be noted that the multiple layer or multiple part molding or casting process executed under the control of computer 24 by the assembly illustrated in FIG. 33 can be alternatively implemented by the furnace assembly of FIG. 31. In that case, container 758 communicates at an inlet with reservoirs of different materials (not illustrated). The contents of the reservoirs flow into container 758 at different times via a valve (not shown) operated by computer 24. The open intervals of the valve are preferably controlled to limit the amounts of the respective liquid dental materials flowing into container 758 at different stages in a molding or casting operation. In that case, the temperature of furnace 752 and the energization of heating elements 754 and 756 are monitored and controlled by computer 24 in accordance with the type of dental material and the stage of the manufacturing process. After forming a first layer of a prosthetic appliance, the furnace is allowed to cool for a predetermined period of time to allow for sufficient hardening of that first layer. Prior to application of a subsequent layer, furnace 752 is again heated, to an appropriate temperature.

The different layers of materials in the case of a dental laboratory exemplarily include a metal or alloy sublayer or superstructure and a porcelain overcoat. The furnace in such an example must of course be sufficiently powerful to handle liquid metal or alloy.

It is to be understood that upper mold support 786 (FIG. 31) may carry different male mold components for different stages of the process. Alternatively, several upper mold components such as illustrated in FIG. 33 may be utilized in the furnace assembly of FIG. 31.

A particularly efficient method for preparing dental appliances involves the cooperation of dental offices, dental laboratories and a central manufacturer, as described hereinabove with respect to the embodiments of FIGS. 18, 26 and 27. The dental laboratories and/or the individual dental offices transmit to the central manufacturer electrical signals encoding geometric specifications of a plurality of dental prostheses, the specifications including dimensions and shapes of tooth preparations at dental sites at which the prostheses are to be affixed and configurations of the prostheses. From the three-dimensional surface data received from the dental offices and/or laboratories, a computer at the central manufacturing facility calculates geometric specifications of a common nearest net shape from which all of the plurality of dental prostheses may be machined. Such a common nearest net shape is generally larger than all the mold components specified by the electrical signals from the dental offices and the laboratories. Accordingly, all the mold components can be machined from the common nearest net shape.

Upon completion of the step of calculating, a pair of mold components is automatically selected as described above to produce, in cooperation with one another, a mold cavity having dimensions and configuration corresponding at least substantially to dimensions and configuration of the common nearest net shape. The selected mold components are automatically placed in predetermined relative positions, as described above, to form the mold cavity. A quantity of a fluidic solidifiable dental material is then introduced into the mold cavity, for example, into the female mold component prior to formation of the mold cavity. A prosthesis form is subsequently removed from the mold cavity upon solidification of the dental material with which the mold cavity is filled.

The prosthesis forms having the common nearest net shape are then shipped to the various laboratories for finishing operations. Specifically, the prosthesis forms are machined or milled by the laboratories. And outer layers such as porcelain coatings may be added. An electronic codification of the dimensions and configuration of the common prosthesis form is conveyed to the laboratories together with the individual forms.

Figure 34:
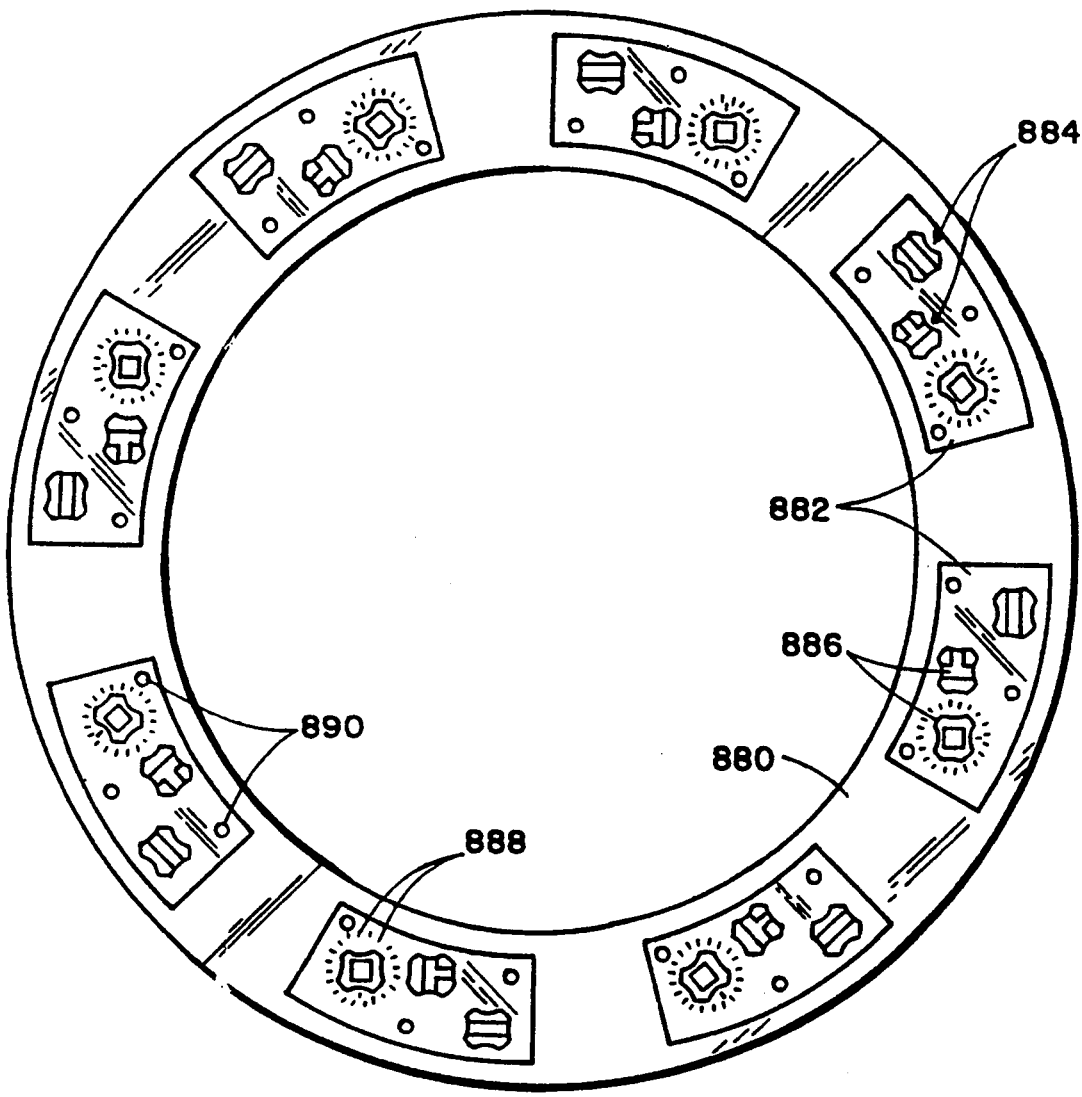
FIG. 34 is a schematic top plan view of an annular holder with a plurality of mold supports carrying respective mold components, in accordance with the present invention.

As illustrated in FIG. 34, a particularly effective mold support assembly for use by a manufacturer comprises an annular mold holder 880 carrying a plurality of arcuate mold supports 882 similar to mold holder 376 in FIG. 22. Mold supports 882 are each provided with one or more holder stations 884 for the insertion of respective mold components 886. In addition, each mold support 882 is formed with a plurality of markers, for example, in the form of a circular array of radially oriented line segments 888, for providing a distance reference for the prosthesis form. Support 882 is shipped to a dental lab together with the mold component(s) 886. In accordance with this scenario, each support 882 holds mold components 886 destined for a particular laboratory. The mold components 886 may be placed on the particular mold support 882 either prior to the molding process or subsequently. Each mold support 882 and the mold components 886 carried thereby are shipped to the laboratories together with a cooperating mold support and associated mold component(s) and the common nearest net shape(s) formed during the molding process. The laboratories can then machine the mold components to produce the exact tooth restoration and tooth preparation surfaces on the mold components. The machined mold components are then used to press the nearest net shapes into final forms for insertion into patients' dentition. Marker lines 888 facilitate the machining of the mold components 886 by providing a laboratory with distance and coordinate references.

Supports 882 are also provided with alignment elements such as bores 890 for guiding the support 882 into a predetermined relationship with a machining apparatus.

It is to be noted that the use of line segments 888 and alignment bores 890 will also provide references and alignment means in the event that supports 882 are used to hold molded preforms or common nearest net shapes. In that event, there is no further press molding and instead the machining operations are performed directly on the dental prosthesis forms, rather than on the mold components.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for use in preparing dental appliances, comprising the steps of:

automatically receiving a plurality of electrical signals encoding geometric specifications of a plurality of dental prostheses, said specifications including dimensions and shape of tooth preparations at dental sites at which said prostheses are to be affixed and configuration of said prostheses;

automatically calculating from said geometric specifications additional geometric specifications of a common nearest net shape from which all of said plurality of dental prostheses may be machined;

upon completing said step of calculating, providing a pair of mold components to produce, in cooperation with one another, a mold cavity having dimensions and configuration corresponding at least substantially to dimensions and configuration of said common nearest net shape;

operating a robotic device to automatically place said first mold component and said second mold component in predetermined relative positions to form said mold cavity;

automatically introducing into said mold cavity a quantity of a fluidic solidifiable dental material; and removing a prosthesis form from said mold cavity upon solidification of the dental material with which said mold cavity is filled.

2. The method defined in claim 1, further comprising the step of shipping said prosthesis form to a user for machining of said prosthesis form by said user.

3. The method defined in claim 2, further comprising the step of conveying to said user an electronic codification of the dimensions and configuration of said prosthesis form.

4. The method defined in claim 2, further comprising the step of removably attaching said prosthesis form to a support having marking means for providing a distance reference for said prosthesis form, said support being shipped to said user with said prosthesis form.

5. The method defined in claim 4 wherein said support is provided with alignment means for guiding said support molded form into a predetermined relationship with a machining apparatus.

* * * * *